United States Patent
Aluru et al.

(10) Patent No.: US 9,254,166 B2
(45) Date of Patent: Feb. 9, 2016

(54) SYSTEMS AND METHODS FOR TURBINATE REDUCTION

(71) Applicant: ArthroCare Corporation, Austin, TX (US)

(72) Inventors: Rajitha Aluru, Austin, TX (US); Doug Evans, Austin, TX (US); David A. Cox, Austin, TX (US); Jean Woloszko, Austin, TX (US); Johnson E. Goode, Austin, TX (US); Philip M. Tetzlaff, Austin, TX (US); Gerardo Molina, Leander, TX (US)

(73) Assignee: ArthroCare Corporation, Austin, TX (US)

( * ) Notice: Subject to any disclaimer, the term of this patent is extended or adjusted under 35 U.S.C. 154(b) by 332 days.

(21) Appl. No.: 13/743,480

(22) Filed: Jan. 17, 2013

(65) Prior Publication Data

US 2014/0200581 A1 Jul. 17, 2014

(51) Int. Cl.
*A61B 18/14* (2006.01)
*A61B 18/04* (2006.01)
*A61B 18/00* (2006.01)

(52) U.S. Cl.
CPC ............. *A61B 18/14* (2013.01); *A61B 18/042* (2013.01); *A61B 18/148* (2013.01); *A61B 18/1477* (2013.01); *A61B 2018/00327* (2013.01);

(Continued)

(58) Field of Classification Search
CPC .. A61B 18/14; A61B 18/042; A61B 18/1477; A61B 18/148; A61B 2018/00327; A61B 2218/007; A61B 2018/1412; A61B 2018/1425; A61B 2018/1427; A61B 2018/00583; A61B 2218/002
See application file for complete search history.

(56) References Cited

U.S. PATENT DOCUMENTS

| 2,050,904 A | 8/1936 | Talley ........................... 219/233 |
| 2,056,377 A | 10/1939 | Wappler ....................... 125/303 |

(Continued)

FOREIGN PATENT DOCUMENTS

| DE | 3930451 A1 | 3/1991 | ............. A61B 17/39 |
| EP | 0509670 | 10/1992 | ............. A61B 17/39 |

(Continued)

OTHER PUBLICATIONS

Barry et al., "The Effect of Radiofrequency-generated Thermal Energy on the Mechanical and Histologic Characteristics of the Arterial Wall in Vivo: Implications of Radiofrequency Angioplasty" *American Heart Journal* vol. 117, pp. 332-341, 1982.

(Continued)

*Primary Examiner* — Catherine Voorhees
(74) *Attorney, Agent, or Firm* — David A. Warmbold

(57) ABSTRACT

The present disclosure includes an electrosurgical apparatus for treating tissue at a target site. The apparatus has a shaft with a proximal end and a distal portion, the distal portion comprising a return electrode and electrode support. There is also at least one active electrode on the shaft distal portion, which has a proximal portion and a distal portion and a plurality of aspiration apertures disposed therebetween. These apertures are fluidly connected to a fluid aspiration cavity that is located within the electrode support, and the cavity is connected with a fluid aspiration element that is located along the shaft. The plurality of apertures vary in size and are generally arranged so that the larger sized apertures are disposed towards the electrode proximal portion and the smaller sized apertures are generally located towards the electrode distal portion.

31 Claims, 8 Drawing Sheets

(52) U.S. Cl.
CPC .............. *A61B2018/00583* (2013.01); *A61B 2018/1412* (2013.01); *A61B 2018/1425* (2013.01); *A61B 2018/1427* (2013.01); *A61B 2218/002* (2013.01); *A61B 2218/007* (2013.01)

(56) References Cited

U.S. PATENT DOCUMENTS

| | | | | |
|---|---|---|---|---|
| 3,633,425 | A | 1/1972 | Sanford | 73/356 |
| 3,815,604 | A | 6/1974 | O'Malley et al. | 128/305 |
| 3,828,780 | A | 8/1974 | Morrison, Jr. et al. | 128/275 |
| 3,901,242 | A | 8/1975 | Storz | 128/303 |
| 3,920,021 | A | 11/1975 | Hiltebrandt | 128/303 |
| 3,939,839 | A | 2/1976 | Curtiss | 128/303 |
| 3,970,088 | A | 7/1976 | Morrison | 128/303 |
| 4,033,351 | A | 7/1977 | Hetzel | 606/48 |
| 4,040,426 | A | 8/1977 | Morrison, Jr. | 128/303 |
| 4,043,342 | A | 8/1977 | Morrison, Jr. | 128/303 |
| 4,074,718 | A | 2/1978 | Morrison, Jr. | 128/303 |
| 4,092,986 | A | 6/1978 | Schneiderman | 128/303 |
| 4,116,198 | A | 9/1978 | Roos | 128/303 |
| 4,181,131 | A | 1/1980 | Ogiu | 128/303 |
| 4,184,492 | A | 1/1980 | Meinke et al. | 128/303 |
| 4,202,337 | A | 5/1980 | Hren et al. | 128/303 |
| 4,228,800 | A | 10/1980 | Degler, Jr. et al. | 128/303 |
| 4,232,676 | A | 11/1980 | Herczog | 128/303 |
| 4,248,231 | A | 2/1981 | Herczog et al. | 128/303 |
| 4,301,802 | A | 11/1981 | Poler | 606/48 |
| 4,326,529 | A | 4/1982 | Doss et al. | 128/303 |
| 4,381,007 | A | 4/1983 | Doss | 128/303 |
| 4,474,179 | A | 10/1984 | Koch | 606/40 |
| 4,476,862 | A | 10/1984 | Pao | 128/303 |
| 4,532,924 | A | 8/1985 | Auth et al. | 128/303 |
| 4,548,207 | A | 10/1985 | Reimels | 128/303 |
| 4,567,890 | A | 2/1986 | Ohta et al. | 128/303 |
| 4,582,057 | A | 4/1986 | Auth et al. | 606/31 |
| 4,590,934 | A | 5/1986 | Malis et al. | 128/303 |
| 4,593,691 | A | 6/1986 | Lindstrom et al. | 128/303 |
| 4,658,817 | A | 4/1987 | Hardy | 606/14 |
| 4,660,571 | A | 4/1987 | Hess et al. | 128/784 |
| 4,674,499 | A | 6/1987 | Pao | 128/303 |
| 4,682,596 | A | 7/1987 | Bales et al. | 128/303 |
| 4,706,667 | A | 11/1987 | Roos | 128/303 |
| 4,709,698 | A | 12/1987 | Johnston et al. | 606/41 |
| 4,727,874 | A | 3/1988 | Bowers et al. | 128/303 |
| 4,765,331 | A | 8/1988 | Petruzzi et al. | 128/303 |
| 4,785,823 | A | 11/1988 | Eggers et al. | 128/692 |
| 4,805,616 | A | 2/1989 | Pao | 128/303 |
| 4,823,791 | A | 4/1989 | D'Amelio et al. | 123/303 |
| 4,832,048 | A | 5/1989 | Cohen | 128/786 |
| 4,860,752 | A | 8/1989 | Turner | 607/102 |
| 4,907,589 | A | 3/1990 | Cosman | 606/34 |
| 4,920,978 | A | 5/1990 | Colvin | 128/784 |
| 4,931,047 | A | 6/1990 | Broadwin et al. | 604/22 |
| 4,936,281 | A | 6/1990 | Stasz | 128/660 |
| 4,936,301 | A | 6/1990 | Rexroth et al. | 606/45 |
| 4,943,290 | A | 7/1990 | Rexroth et al. | 606/45 |
| 4,966,597 | A | 10/1990 | Cosman | 606/50 |
| 4,967,765 | A | 11/1990 | Turner et al. | 128/785 |
| 4,976,711 | A | 12/1990 | Parins et al. | 606/48 |
| 4,979,948 | A | 12/1990 | Geddes et al. | 606/33 |
| 4,998,933 | A | 3/1991 | Eggers et al. | 606/41 |
| 5,007,908 | A | 4/1991 | Rydell | 606/47 |
| 5,009,656 | A | 4/1991 | Reimels | 606/48 |
| 5,035,696 | A | 7/1991 | Rydell | 606/47 |
| 5,047,026 | A | 9/1991 | Rydell | 606/48 |
| 5,047,027 | A | 9/1991 | Rydell | 606/48 |
| 5,057,105 | A | 10/1991 | Malone et al. | 606/28 |
| 5,057,106 | A | 10/1991 | Kasevich et al. | 606/33 |
| 5,078,716 | A | 1/1992 | Doll | 606/47 |
| 5,078,717 | A | 1/1992 | Parins et al. | 606/48 |
| 5,080,660 | A | 1/1992 | Buelna | 606/45 |
| 5,083,565 | A | 1/1992 | Parins | 600/374 |
| 5,084,044 | A | 1/1992 | Quint | 606/27 |
| 5,085,659 | A | 2/1992 | Rydell | 606/47 |
| 5,088,997 | A | 2/1992 | Delahuerga et al. | 606/42 |
| 5,098,431 | A | 3/1992 | Rydell | 606/48 |
| 5,099,840 | A | 3/1992 | Goble | 128/422 |
| 5,102,410 | A | 4/1992 | Dressel | 606/15 |
| 5,108,391 | A | 4/1992 | Flachenecker et al. | 606/38 |
| RE33,925 | E | 5/1992 | Bales et al. | 606/48 |
| 5,112,330 | A | 5/1992 | Nishigaki et al. | 606/46 |
| 5,122,138 | A | 6/1992 | Manwaring | 606/46 |
| 5,125,928 | A | 6/1992 | Parins et al. | 606/48 |
| 5,156,151 | A | 10/1992 | Imran | 600/375 |
| 5,167,659 | A | 12/1992 | Ohtomo et al. | 606/40 |
| 5,167,660 | A | 12/1992 | Altendorf | 606/40 |
| 5,171,311 | A | 12/1992 | Rydell et al. | 606/48 |
| 5,178,620 | A | 1/1993 | Eggers et al. | 606/41 |
| 5,190,517 | A | 3/1993 | Zieve et al. | 604/22 |
| 5,192,280 | A | 3/1993 | Parins | 606/48 |
| 5,195,959 | A | 3/1993 | Smith | 604/34 |
| 5,195,968 | A | 3/1993 | Lundquist et al. | 604/95.04 |
| 5,196,007 | A | 3/1993 | Ellman | 606/32 |
| 5,197,466 | A | 3/1993 | Marchosky et al. | 128/399 |
| 5,197,963 | A | 3/1993 | Parins | 606/46 |
| 5,207,675 | A | 5/1993 | Canady | 606/40 |
| 5,217,457 | A | 6/1993 | Delahuerga et al. | 606/42 |
| 5,217,459 | A | 6/1993 | Kamerling | 606/48 |
| 5,249,585 | A | 10/1993 | Turner et al. | 607/99 |
| 5,261,410 | A | 11/1993 | Alfano et al. | 600/475 |
| 5,267,994 | A | 12/1993 | Gentelia et al. | 606/15 |
| 5,267,997 | A | 12/1993 | Farin et al. | 606/38 |
| 5,273,524 | A | 12/1993 | Fox et al. | 604/21 |
| 5,277,201 | A | 1/1994 | Stern | 607/98 |
| 5,281,216 | A | 1/1994 | Klicek | 606/42 |
| 5,281,218 | A | 1/1994 | Imran | 606/41 |
| 5,290,282 | A | 3/1994 | Casscells | 606/29 |
| 5,300,069 | A | 4/1994 | Hunsberger et al. | 606/37 |
| 5,306,238 | A | 4/1994 | Fleenor | 606/42 |
| 5,312,400 | A | 5/1994 | Bales et al. | 606/41 |
| 5,314,406 | A | 5/1994 | Arias et al. | 604/21 |
| 5,324,254 | A | 6/1994 | Phillips | 604/21 |
| 5,330,470 | A | 7/1994 | Hagen | 606/42 |
| 5,334,140 | A | 8/1994 | Phillips | 604/35 |
| 5,334,183 | A | 8/1994 | Wuchinich | 606/46 |
| 5,334,193 | A | 8/1994 | Nardella | 606/41 |
| 5,336,220 | A | 8/1994 | Ryan et al. | 604/22 |
| 5,336,443 | A | 8/1994 | Odashima | 252/511 |
| 5,342,357 | A | 8/1994 | Nardella | 606/40 |
| 5,363,861 | A | 11/1994 | Edwards et al. | 600/585 |
| 5,366,443 | A | 11/1994 | Eggers et al. | 604/114 |
| 5,370,675 | A | 12/1994 | Edwards et al. | 607/101 |
| 5,374,261 | A | 12/1994 | Yoon | 604/385.01 |
| 5,375,588 | A | 12/1994 | Yoon | 128/4 |
| 5,380,277 | A | 1/1995 | Phillips | 604/33 |
| 5,380,316 | A | 1/1995 | Aita | 606/7 |
| 5,383,876 | A | 1/1995 | Nardella | 606/49 |
| 5,383,917 | A | 1/1995 | Desai et al. | 607/702 |
| 5,389,096 | A | 2/1995 | Aita | 606/15 |
| 5,395,312 | A | 3/1995 | Desai | 604/22 |
| 5,395,363 | A | 3/1995 | Billings et al. | 606/41 |
| 5,395,368 | A | 3/1995 | Ellman et al. | 606/45 |
| 5,400,267 | A | 3/1995 | Denen et al. | 702/59 |
| 5,401,272 | A | 3/1995 | Perkins | 606/15 |
| 5,403,311 | A | 4/1995 | Abele et al. | 606/49 |
| 5,417,687 | A | 5/1995 | Nardella et al. | 606/32 |
| 5,419,767 | A | 5/1995 | Eggers et al. | 604/114 |
| 5,423,810 | A | 6/1995 | Goble et al. | 606/40 |
| 5,423,811 | A | 6/1995 | Imran et al. | 606/41 |
| 5,423,812 | A | 6/1995 | Ellman et al. | 606/45 |
| 5,423,882 | A | 6/1995 | Jackman et al. | 607/122 |
| 5,436,566 | A | 7/1995 | Thompson et al. | 324/713 |
| 5,437,662 | A | 8/1995 | Nardella | 606/40 |
| 5,438,302 | A | 8/1995 | Goble | 331/167 |
| 5,441,499 | A | 8/1995 | Fritzsch | 606/45 |
| 5,451,224 | A | 9/1995 | Goble et al. | 606/48 |
| 5,454,809 | A | 10/1995 | Janssen | 606/41 |
| 5,456,662 | A | 10/1995 | Edwards et al. | 604/22 |
| 5,458,596 | A | 10/1995 | Lax et al. | 606/31 |
| 5,487,757 | A | 1/1996 | Truckai et al. | 604/264 |
| 5,490,850 | A | 2/1996 | Ellman et al. | 606/45 |
| 5,496,312 | A | 3/1996 | Klicek | 606/34 |
| 5,496,314 | A | 3/1996 | Eggers | 606/41 |
| 5,496,317 | A | 3/1996 | Goble et al. | 606/48 |

(56) References Cited

U.S. PATENT DOCUMENTS

| | | | | |
|---|---|---|---|---|
| 5,505,728 | A | 4/1996 | Ellman et al. | 606/39 |
| 5,505,730 | A | 4/1996 | Edwards | 606/41 |
| 5,514,130 | A | 5/1996 | Baker | 606/41 |
| 5,554,152 | A | 9/1996 | Aita | 606/7 |
| 5,556,397 | A | 9/1996 | Long et al. | 606/48 |
| 5,562,503 | A | 10/1996 | Ellman et al. | 439/638 |
| 5,562,703 | A | 10/1996 | Desai | 606/210 |
| 5,569,242 | A | 10/1996 | Lax et al. | 606/42 |
| 5,571,100 | A | 11/1996 | Goble et al. | 606/41 |
| 5,571,101 | A | 11/1996 | Ellman et al. | 606/45 |
| 5,584,872 | A | 12/1996 | LaFontaine et al. | 607/117 |
| 5,609,151 | A | 3/1997 | Mulier et al. | 128/642 |
| 5,624,439 | A | 4/1997 | Edwards et al. | 606/45 |
| 5,630,812 | A | 5/1997 | Ellman et al. | 606/41 |
| 5,633,578 | A | 5/1997 | Eggers et al. | 323/301 |
| 5,647,869 | A | 7/1997 | Goble et al. | 606/37 |
| 5,658,278 | A | 8/1997 | Imran et al. | 606/41 |
| 5,662,680 | A | 9/1997 | Desai | 606/210 |
| 5,674,191 | A | 10/1997 | Edwards et al. | 604/22 |
| 5,676,693 | A | 10/1997 | LaFontaine et al. | 607/116 |
| 5,681,282 | A | 10/1997 | Eggers et al. | 604/114 |
| 5,683,366 | A | 11/1997 | Eggers et al. | 604/114 |
| 5,683,386 | A | 11/1997 | Ellman et al. | 606/41 |
| 5,683,387 | A | 11/1997 | Garito et al. | 606/45 |
| 5,688,267 | A | 11/1997 | Panescu et al. | 606/41 |
| 5,695,495 | A | 12/1997 | Ellman et al. | 606/41 |
| 5,697,281 | A | 12/1997 | Eggers et al. | 604/114 |
| 5,697,536 | A | 12/1997 | Eggers et al. | 604/114 |
| 5,697,882 | A | 12/1997 | Eggers et al. | 604/114 |
| 5,697,909 | A | 12/1997 | Eggers et al. | 604/114 |
| 5,700,262 | A | 12/1997 | Acosta et al. | 606/48 |
| 5,707,349 | A | 1/1998 | Edwards | 604/22 |
| 5,718,702 | A | 2/1998 | Edwards | 606/41 |
| 5,725,524 | A | 3/1998 | Mulier et al. | 606/41 |
| 5,728,094 | A | 3/1998 | Edwards | 606/41 |
| 5,733,282 | A | 3/1998 | Ellman et al. | 606/45 |
| 5,738,114 | A | 4/1998 | Edwards | 128/898 |
| 5,743,870 | A | 4/1998 | Edwards | 604/22 |
| 5,746,224 | A | 5/1998 | Edwards | 128/898 |
| 5,749,869 | A | 5/1998 | Lindenmeier et al. | 606/34 |
| 5,766,153 | A | 6/1998 | Eggers et al. | 604/114 |
| 5,775,338 | A | 7/1998 | Hastings | 128/898 |
| 5,776,128 | A | 7/1998 | Eggers | 606/48 |
| 5,782,828 | A | 7/1998 | Chen et al. | 606/42 |
| 5,800,379 | A | 9/1998 | Edwards | 604/22 |
| 5,800,429 | A | 9/1998 | Edwards | 606/41 |
| 5,807,395 | A | 9/1998 | Mulier et al. | 606/41 |
| 5,810,764 | A | 9/1998 | Eggers et al. | 604/23 |
| 5,810,809 | A | 9/1998 | Rydell | 606/49 |
| 5,817,049 | A | 10/1998 | Edwards | 604/22 |
| 5,820,580 | A | 10/1998 | Edwards et al. | 604/22 |
| 5,823,197 | A | 10/1998 | Edwards | 128/898 |
| 5,827,277 | A | 10/1998 | Edwards | 606/41 |
| 5,836,875 | A | 11/1998 | Webster, Jr. | 600/374 |
| 5,843,019 | A | 12/1998 | Eggers et al. | 604/22 |
| 5,843,021 | A | 12/1998 | Edwards et al. | 604/22 |
| 5,843,077 | A | 12/1998 | Edwards | 606/41 |
| 5,860,951 | A | 1/1999 | Eggers | 604/510 |
| 5,860,974 | A | 1/1999 | Abele | 606/41 |
| 5,860,975 | A | 1/1999 | Goble et al. | 606/45 |
| 5,871,469 | A | 2/1999 | Eggers et al. | 604/114 |
| 5,873,855 | A | 2/1999 | Eggers et al. | 604/114 |
| 5,879,349 | A | 3/1999 | Edwards | 606/45 |
| 5,885,277 | A | 3/1999 | Korth | 606/35 |
| 5,888,198 | A | 3/1999 | Eggers et al. | 604/114 |
| 5,891,095 | A | 4/1999 | Eggers et al. | 604/114 |
| 5,891,134 | A | 4/1999 | Goble et al. | 606/27 |
| 5,897,553 | A | 4/1999 | Mulier | 606/41 |
| 5,902,272 | A | 5/1999 | Eggers et al. | 604/114 |
| 5,916,214 | A | 6/1999 | Cosio et al. | 606/41 |
| 5,919,190 | A | 7/1999 | Vandusseldorp | 606/46 |
| 5,921,983 | A | 7/1999 | Shannon, Jr. | 606/45 |
| 5,944,715 | A | 8/1999 | Goble et al. | 606/41 |
| 5,954,716 | A | 9/1999 | Sharkey et al. | 606/32 |
| 5,988,171 | A | 11/1999 | Sohn et al. | 128/848 |
| 6,004,319 | A | 12/1999 | Goble et al. | 606/48 |
| 6,006,755 | A | 12/1999 | Edwards | 128/898 |
| 6,009,877 | A | 1/2000 | Edwards | 128/898 |
| 6,013,076 | A | 1/2000 | Goble et al. | 606/41 |
| 6,015,406 | A | 1/2000 | Goble et al. | 606/41 |
| 6,024,733 | A | 2/2000 | Eggers et al. | 604/500 |
| 6,026,816 | A | 2/2000 | McMillan et al. | 128/898 |
| 6,027,501 | A | 2/2000 | Goble et al. | 606/41 |
| 6,039,734 | A | 3/2000 | Goble et al. | 606/41 |
| 6,044,846 | A | 4/2000 | Edwards | 128/898 |
| 6,047,700 | A | 4/2000 | Eggers et al. | 128/898 |
| 6,053,172 | A * | 4/2000 | Hovda et al. | 128/898 |
| 6,056,746 | A | 5/2000 | Goble et al. | 606/48 |
| 6,063,079 | A | 5/2000 | Hovda et al. | 606/41 |
| 6,066,134 | A | 5/2000 | Eggers et al. | 606/32 |
| 6,066,139 | A | 5/2000 | Ryan et al. | 606/50 |
| 6,068,628 | A | 5/2000 | Fanton et al. | 606/41 |
| 6,071,281 | A | 6/2000 | Burnside et al. | 606/41 |
| 6,073,052 | A | 6/2000 | Zelickson et al. | 607/100 |
| 6,074,386 | A | 6/2000 | Goble et al. | 606/34 |
| 6,086,585 | A | 7/2000 | Hovda et al. | 606/45 |
| 6,090,106 | A | 7/2000 | Goble et al. | 606/41 |
| 6,093,186 | A | 7/2000 | Goble et al. | 606/34 |
| 6,102,046 | A | 8/2000 | Weinstein et al. | 128/898 |
| 6,105,581 | A | 8/2000 | Eggers et al. | 128/898 |
| 6,109,268 | A | 8/2000 | Thapliyal et al. | 128/898 |
| 6,117,109 | A | 9/2000 | Eggers et al. | 604/114 |
| 6,126,682 | A | 10/2000 | Sharkey et al. | 607/96 |
| 6,142,992 | A | 11/2000 | Cheng et al. | 606/34 |
| 6,149,620 | A | 11/2000 | Baker et al. | 604/22 |
| 6,159,194 | A | 12/2000 | Eggers et al. | 604/500 |
| 6,159,208 | A | 12/2000 | Hovda et al. | 606/41 |
| 6,168,593 | B1 | 1/2001 | Sharkey et al. | 606/34 |
| 6,174,309 | B1 | 1/2001 | Wrublewski et al. | 606/45 |
| 6,179,824 | B1 | 1/2001 | Eggers et al. | 604/500 |
| 6,179,836 | B1 | 1/2001 | Eggers et al. | 606/45 |
| 6,183,469 | B1 | 2/2001 | Thapliyal et al. | 606/41 |
| 6,190,381 | B1 | 2/2001 | Olsen et al. | 606/32 |
| 6,203,542 | B1 | 3/2001 | Ellsberry et al. | 606/41 |
| 6,210,402 | B1 | 4/2001 | Olsen et al. | 606/32 |
| 6,210,405 | B1 | 4/2001 | Goble et al. | 606/41 |
| 6,224,592 | B1 | 5/2001 | Eggers et al. | 606/32 |
| 6,228,078 | B1 | 5/2001 | Eggers | 606/32 |
| 6,228,081 | B1 | 5/2001 | Goble | 606/34 |
| 6,234,178 | B1 | 5/2001 | Goble et al. | 128/898 |
| 6,235,020 | B1 | 5/2001 | Cheng et al. | 606/34 |
| 6,237,604 | B1 | 5/2001 | Burnside et al. | 128/897 |
| 6,238,391 | B1 | 5/2001 | Olsen et al. | 606/41 |
| 6,254,600 | B1 | 7/2001 | Willink et al. | 606/41 |
| 6,258,086 | B1 | 7/2001 | Ashley et al. | 606/41 |
| 6,261,286 | B1 | 7/2001 | Goble et al. | 606/34 |
| 6,261,311 | B1 | 7/2001 | Sharkey et al. | 607/96 |
| 6,264,652 | B1 | 7/2001 | Eggers et al. | 606/41 |
| 6,270,460 | B1 | 8/2001 | McCartan et al. | 600/459 |
| 6,270,476 | B1 | 8/2001 | Santoianni et al. | 604/95.04 |
| 6,277,112 | B1 | 8/2001 | Underwood et al. | 606/32 |
| 6,280,441 | B1 | 8/2001 | Ryan | 606/45 |
| 6,283,961 | B1 | 9/2001 | Underwood et al. | 606/41 |
| 6,293,942 | B1 | 9/2001 | Goble et al. | 606/38 |
| 6,296,636 | B1 | 10/2001 | Cheng et al. | 606/32 |
| 6,296,638 | B1 | 10/2001 | Davison et al. | 606/41 |
| 6,306,134 | B1 | 10/2001 | Goble et al. | 606/42 |
| 6,308,089 | B1 | 10/2001 | von der Rur et al. | 600/338 |
| 6,309,387 | B1 | 10/2001 | Eggers et al. | 606/41 |
| 6,312,408 | B1 | 11/2001 | Eggers et al. | 604/114 |
| 6,322,549 | B1 | 11/2001 | Eggers et al. | 604/500 |
| 6,355,032 | B1 | 3/2002 | Hovda et al. | 606/32 |
| 6,363,937 | B1 | 4/2002 | Hovda et al. | 128/898 |
| 6,364,877 | B1 | 4/2002 | Goble et al. | 606/34 |
| 6,379,350 | B1 | 4/2002 | Sharkey et al. | 606/41 |
| 6,379,351 | B1 | 4/2002 | Thapliyal et al. | 606/41 |
| 6,387,093 | B1 | 5/2002 | Ellman et al. | 606/39 |
| 6,391,025 | B1 | 5/2002 | Weinstein et al. | 606/41 |
| 6,411,852 | B1 | 6/2002 | Danek et al. | 607/42 |
| 6,413,254 | B1 | 7/2002 | Hissong et al. | 606/27 |
| 6,416,491 | B1 | 7/2002 | Edwards et al. | 606/41 |
| 6,416,507 | B1 | 7/2002 | Eggers et al. | 606/32 |
| 6,416,508 | B1 | 7/2002 | Eggers et al. | 606/32 |
| 6,416,509 | B1 | 7/2002 | Goble et al. | 606/37 |

(56) References Cited

U.S. PATENT DOCUMENTS

| | | | |
|---|---|---|---|
| 6,427,089 B1 | 7/2002 | Knowlton | 607/101 |
| 6,432,103 B1 | 8/2002 | Ellsberry et al. | 606/41 |
| 6,464,699 B1 | 10/2002 | Swanson | 606/41 |
| 6,468,274 B1 | 10/2002 | Alleyne et al. | 606/32 |
| 6,468,275 B1 | 10/2002 | Wampler et al. | 606/48 |
| 6,482,201 B1 | 11/2002 | Olsen et al. | 606/41 |
| 6,491,690 B1 | 12/2002 | Goble et al. | 606/41 |
| 6,517,498 B1 | 2/2003 | Burbank et al. | 600/564 |
| 6,530,922 B2 | 3/2003 | Cosman | 606/34 |
| 6,530,924 B1 | 3/2003 | Ellman et al. | 606/45 |
| 6,551,032 B1 | 4/2003 | Nolan et al. | 407/13 |
| 6,572,613 B1 | 6/2003 | Ellman et al. | 606/45 |
| 6,578,579 B2 | 6/2003 | Burnside | 128/897 |
| 6,589,235 B2 | 7/2003 | Wong et al. | 606/32 |
| 6,589,237 B2 | 7/2003 | Woloszko et al. | 606/41 |
| 6,602,248 B1 | 8/2003 | Sharps et al. | 606/32 |
| 6,620,156 B1 | 9/2003 | Garito et al. | 606/50 |
| 6,632,193 B1 | 10/2003 | Davison et al. | 604/22 |
| 6,632,220 B1 | 10/2003 | Eggers et al. | 606/41 |
| 6,702,810 B2 | 3/2004 | McClurken et al. | 606/34 |
| 6,736,810 B2 | 5/2004 | Hoey et al. | 606/34 |
| 6,746,447 B2 | 6/2004 | Davison et al. | 606/41 |
| 6,749,604 B1 | 6/2004 | Eggers et al. | 606/41 |
| 6,749,608 B2 | 6/2004 | Garito et al. | 606/45 |
| 6,770,071 B2 | 8/2004 | Woloszko et al. | 606/41 |
| 6,780,178 B2 | 8/2004 | Palanker et al. | 600/41 |
| 6,780,180 B1 | 8/2004 | Goble et al. | 606/41 |
| 6,802,842 B2 | 10/2004 | Ellman et al. | 606/45 |
| 6,837,887 B2 | 1/2005 | Woloszko et al. | 606/41 |
| 6,837,888 B2 | 1/2005 | Ciarrocca et al. | 606/41 |
| 6,920,883 B2 | 7/2005 | Bessette et al. | 128/898 |
| 6,929,640 B1 | 8/2005 | Underwood et al. | 606/32 |
| 6,942,662 B2 | 9/2005 | Goble et al. | 606/48 |
| 6,949,096 B2 | 9/2005 | Davison et al. | 606/41 |
| 6,955,172 B2 | 10/2005 | Nelson et al. | 128/848 |
| 6,960,204 B2 | 11/2005 | Eggers et al. | 606/32 |
| 6,974,453 B2 | 12/2005 | Woloszko et al. | 606/41 |
| 6,984,231 B2 | 1/2006 | Goble et al. | 606/37 |
| 6,991,631 B2 | 1/2006 | Woloszko et al. | 606/41 |
| 7,004,941 B2 | 2/2006 | Tvinnereim et al. | 606/41 |
| 7,041,102 B2 | 5/2006 | Truckai et al. | 606/51 |
| 7,066,936 B2 | 6/2006 | Ryan | 606/45 |
| 7,070,596 B1 | 7/2006 | Woloszko et al. | 606/41 |
| 7,090,672 B2 | 8/2006 | Underwood et al. | 606/41 |
| 7,094,215 B2 | 8/2006 | Davison et al. | 604/22 |
| 7,104,986 B2 | 9/2006 | Hovda et al. | 606/32 |
| 7,131,969 B1 | 11/2006 | Hovda et al. | 606/45 |
| 7,169,143 B2 | 1/2007 | Eggers et al. | 606/32 |
| 7,179,255 B2 | 2/2007 | Lettice et al. | 606/32 |
| 7,186,234 B2 | 3/2007 | Dahla et al. | 604/22 |
| 7,192,428 B2 | 3/2007 | Eggers et al. | 606/41 |
| 7,195,630 B2 | 3/2007 | Ciarrocca | 606/48 |
| 7,201,750 B1 | 4/2007 | Eggers et al. | 606/41 |
| 7,217,268 B2 | 5/2007 | Eggers et al. | 606/32 |
| 7,241,293 B2 | 7/2007 | Davison | 600/410 |
| 7,270,658 B2 | 9/2007 | Woloszko et al. | 606/32 |
| 7,270,659 B2 | 9/2007 | Ricart et al. | 606/32 |
| 7,270,661 B2 | 9/2007 | Dahla et al. | 606/41 |
| 7,276,063 B2 | 10/2007 | Davison et al. | 606/41 |
| 7,297,143 B2 | 11/2007 | Woloszko et al. | 606/41 |
| 7,297,145 B2 | 11/2007 | Woloszko et al. | 606/41 |
| 7,318,823 B2 | 1/2008 | Sharps et al. | 606/32 |
| 7,331,956 B2 | 2/2008 | Hovda et al. | 606/32 |
| RE40,156 E | 3/2008 | Sharps et al. | 606/32 |
| 7,357,798 B2 | 4/2008 | Sharps et al. | 606/32 |
| 7,387,625 B2 | 6/2008 | Hovda et al. | 606/32 |
| 7,419,488 B2 | 9/2008 | Ciarrocca et al. | 606/41 |
| 7,429,260 B2 | 9/2008 | Underwood et al. | 606/32 |
| 7,429,262 B2 | 9/2008 | Woloszko et al. | 606/46 |
| 7,435,247 B2 | 10/2008 | Woloszko et al. | 604/45 |
| 7,442,191 B2 | 10/2008 | Hovda et al. | 606/41 |
| 7,445,618 B2 | 11/2008 | Eggers et al. | 604/48 |
| 7,449,021 B2 | 11/2008 | Underwood et al. | 606/32 |
| 7,462,178 B2 | 12/2008 | Woloszko et al. | 607/105 |
| 7,468,059 B2 | 12/2008 | Eggers et al. | 606/32 |
| 7,491,200 B2 | 2/2009 | Underwood et al. | 606/32 |
| 7,507,236 B2 | 3/2009 | Eggers et al. | 606/41 |
| 7,572,251 B1 | 8/2009 | Davison et al. | 604/500 |
| 7,632,267 B2 | 12/2009 | Dahla | 606/41 |
| 7,691,101 B2 | 4/2010 | Davison et al. | 606/41 |
| 7,704,249 B2 | 4/2010 | Woloszko et al. | 606/48 |
| 7,708,733 B2 | 5/2010 | Sanders et al. | 606/41 |
| 7,824,398 B2 | 11/2010 | Woloszko et al. | 606/45 |
| 7,879,034 B2 | 2/2011 | Woloszko et al. | 606/48 |
| 7,892,230 B2 | 2/2011 | Woloszko et al. | 606/41 |
| 7,901,403 B2 | 3/2011 | Woloszko et al. | 606/48 |
| 8,012,153 B2 | 9/2011 | Woloszko et al. | 606/48 |
| 8,114,071 B2 | 2/2012 | Woloszko et al. | 606/32 |
| 2002/0029036 A1 | 3/2002 | Goble et al. | 606/38 |
| 2002/0049438 A1 | 4/2002 | Sharkey et al. | 606/41 |
| 2003/0013986 A1 | 1/2003 | Saadat | 600/549 |
| 2003/0014050 A1 | 1/2003 | Sharkey et al. | 606/45 |
| 2003/0088245 A1 | 5/2003 | Woloszko et al. | 606/41 |
| 2003/0097129 A1* | 5/2003 | Davison et al. | 606/41 |
| 2003/0158545 A1 | 8/2003 | Hovda et al. | 606/32 |
| 2003/0171743 A1 | 9/2003 | Tasto et al. | 606/32 |
| 2003/0208196 A1 | 11/2003 | Stone | 606/41 |
| 2003/0212396 A1 | 11/2003 | Eggers et al. | 606/41 |
| 2004/0116922 A1 | 6/2004 | Hovda et al. | 606/41 |
| 2004/0127893 A1 | 7/2004 | Hovda | 606/41 |
| 2004/0230190 A1 | 11/2004 | Dahla et al. | 604/41 |
| 2005/0004634 A1 | 1/2005 | Ricart et al. | 606/41 |
| 2005/0261754 A1 | 11/2005 | Woloszko et al. | 606/32 |
| 2005/0283149 A1 | 12/2005 | Thorne et al. | 606/48 |
| 2006/0036237 A1 | 2/2006 | Davison et al. | 606/41 |
| 2006/0095031 A1 | 5/2006 | Ormsby | 606/34 |
| 2006/0129145 A1* | 6/2006 | Woloszko et al. | 606/41 |
| 2006/0189971 A1 | 8/2006 | Tasto et al. | 606/32 |
| 2006/0253117 A1 | 11/2006 | Hovda et al. | 128/898 |
| 2006/0259025 A1 | 11/2006 | Dahla | 607/108 |
| 2007/0010808 A1* | 1/2007 | Dahla | 606/41 |
| 2007/0106288 A1 | 5/2007 | Woloszko et al. | 606/41 |
| 2007/0149966 A1 | 6/2007 | Dahla et al. | 606/41 |
| 2007/0161981 A1 | 7/2007 | Sanders et al. | 606/41 |
| 2007/0282323 A1* | 12/2007 | Woloszko et al. | 606/41 |
| 2010/0204690 A1 | 8/2010 | Bigley et al. | 606/41 |
| 2012/0101494 A1 | 4/2012 | Cadouri | 606/41 |
| 2012/0191089 A1 | 7/2012 | Gonzalez et al. | 606/45 |
| 2012/0203219 A1 | 8/2012 | Evans et al. | 606/33 |
| 2012/0226273 A1 | 9/2012 | Nguyen et al. | 606/41 |

FOREIGN PATENT DOCUMENTS

| | | | | |
|---|---|---|---|---|
| EP | 0703461 A2 | 3/1996 | | G01B 27/02 |
| EP | 0740926 A2 | 11/1996 | | A61B 17/39 |
| EP | 0754437 A2 | 1/1997 | | A61B 17/39 |
| EP | 0694290 B1 | 11/2000 | | A61B 18/04 |
| EP | 2198799 | 6/2010 | | A61B 18/14 |
| FR | 2313949 | 1/1977 | | A61N 3/02 |
| GB | 2 308 979 | 7/1997 | | A61B 17/36 |
| GB | 2 308 980 | 7/1997 | | A61B 17/36 |
| GB | 2 308 981 | 7/1997 | | A61B 17/36 |
| GB | 2 327 350 | 1/1999 | | A61B 17/39 |
| GB | 2 327 351 | 1/1999 | | A61B 17/39 |
| GB | 2 327 352 | 1/1999 | | A61B 17/39 |
| GB | 2479582 | 10/2011 | | A61B 18/14 |
| JP | 57-57802 | 4/1982 | | A61B 1/00 |
| JP | 57-117843 | 7/1982 | | A61B 17/39 |
| JP | 58-13213 | 1/1983 | | A61B 18/12 |
| JP | 10-43198 | 2/1998 | | A61B 17/42 |
| WO | 90/03152 | 4/1990 | | A61B 17/39 |
| WO | 90/07303 | 7/1990 | | A61B 17/39 |
| WO | 92/21278 | 12/1992 | | A61B 5/04 |
| WO | 93/13816 | 7/1993 | | A61B 17/36 |
| WO | 93/20747 | 10/1993 | | A61B 5/00 |
| WO | 94/04220 | 3/1994 | | A61N 1/06 |
| WO | 94/08654 | 4/1994 | | A61M 37/00 |
| WO | 94/10924 | 5/1994 | | A61B 17/39 |
| WO | 94/26228 | 11/1994 | | A61G 17/36 |
| WO | 95/34259 | 12/1995 | | A61F 5/48 |
| WO | 96/00042 | 1/1996 | | A61B 17/39 |
| WO | 96/23449 | 8/1996 | | A61B 17/39 |
| WO | 96/37156 | 11/1996 | | A61B 17/00 |
| WO | 96/39914 | 12/1996 | | A61B 1/00 |

(56) References Cited

FOREIGN PATENT DOCUMENTS

| WO | 97/00646 | 1/1997 | ............ | A61B 17/39 |
|---|---|---|---|---|
| WO | 97/00647 | 1/1997 | ............ | A61B 17/39 |
| WO | 97/15237 | 5/1997 | ............ | A61B 18/12 |
| WO | 97/18765 | 5/1997 | ............ | A61B 17/36 |
| WO | 97/24073 | 7/1997 | ............ | A61B 17/39 |
| WO | 97/24074 | 7/1997 | ............ | A61B 17/39 |
| WO | 97/24993 | 7/1997 | ............ | A61B 17/39 |
| WO | 97/24994 | 7/1997 | ............ | A61B 17/39 |
| WO | 97/30644 | 8/1997 | ............ | A61B 17/39 |
| WO | 97/30645 | 8/1997 | ............ | A61B 17/39 |
| WO | 97/30646 | 8/1997 | ............ | A61B 17/39 |
| WO | 97/30647 | 8/1997 | ............ | A61B 17/39 |
| WO | 97/41785 | 11/1997 | ............ | A61B 17/39 |
| WO | 97/41786 | 11/1997 | ............ | A61B 17/39 |
| WO | 97/41787 | 11/1997 | ............ | A61B 17/39 |
| WO | 97/41788 | 11/1997 | ............ | A61B 17/39 |
| WO | 97/43969 | 11/1997 | ............ | A61B 17/39 |
| WO | 97/43970 | 11/1997 | ............ | A61B 17/39 |
| WO | 97/43972 | 11/1997 | ............ | A61B 17/39 |
| WO | 97/43973 | 11/1997 | ............ | A61B 17/39 |
| WO | 97/44092 | 11/1997 | ............ | A61B 17/39 |
| WO | 97/48345 | 12/1997 | ............ | A61B 17/39 |
| WO | 97/48346 | 12/1997 | ............ | A61B 17/39 |
| WO | 98/03117 | 1/1998 | ............ | A61B 17/00 |
| WO | 98/07468 | 2/1998 | ............... | A61N 1/40 |
| WO | 98/27879 | 7/1998 | ............ | A61B 17/36 |
| WO | 98/27880 | 7/1998 | ............ | A61B 17/39 |
| WO | 99/08613 | 2/1999 | ............ | A61B 17/36 |
| WO | 99/09919 | 3/1999 | ............ | A61B 18/12 |
| WO | 99/17690 | 4/1999 | ................ | A61F 7/12 |
| WO | 99/30655 | 6/1999 | ................ | A61F 7/12 |
| WO | 99/51155 | 10/1999 | ............ | A61B 17/36 |
| WO | 99/51158 | 10/1999 | ............ | A61B 17/39 |
| WO | 00/62698 | 10/2000 | ............ | A61B 18/14 |
| WO | 01/87154 | 5/2001 | ............... | A61B 5/05 |
| WO | 02/36028 | 5/2002 | ............ | A61B 18/12 |
| WO | 02/085230 | 10/2002 | ............ | A61B 18/14 |
| WO | 03/005882 | 1/2003 | ............ | A61B 18/14 |
| WO | 03/024305 | 3/2003 | | |
| WO | 03/047446 | 6/2003 | ............ | A61B 18/12 |
| WO | 03/068095 | 8/2003 | ............ | A61B 18/14 |
| WO | 2004/050171 | 6/2004 | | |
| WO | 2005/125287 | 12/2005 | ............ | A61B 18/00 |
| WO | 2006/002337 | 1/2006 | ............ | A61B 18/14 |
| WO | 2006/125007 | 11/2006 | ............ | A61B 18/14 |

OTHER PUBLICATIONS

BiLAP Generator Settings, Jun. 1991.
BiLAP IFU 910026-001 Rev A for BiLAP Model 3525, J-Hook, 4 pgs, May 20, 1991.
BiLAP IFU 910033-002 Rev A for BiLAP Model 3527, L-Hook; BiLAP Model 3525, J-Hook; BiLAP Model 3529, High Angle, 2 pgs, Nov. 30, 1993.
Codman & Shurtleff, Inc. "The Malis Bipolar Coagulating and Bipolar Cutting System CMC-II" brochure, early, 2 pgs, 1991.
Codman & Shurtleff, Inc. "The Malis Bipolar Electrosurgical System CMC—III Instruction Manual" , 15 pgs, Jul. 1991.
Cook et al., "Therapeutic Medical Devices: Application and Design" , Prentice Hall, Inc., 3pgs, 1982.
Dennis et al. "Evolution of Electrofulguration in Control of Bleeding of Experimental Gastric Ulcers," Digestive Diseases and Sciences, vol. 24, No. 11, 845-848, Nov. 1979.
Dobbie, A.K., "The Electrical Aspects of Surgical Diathermy, Bio Medical Engineering" Bio-Medical Engineering vol. 4, pp. 206-216, May 1969.
Elsasser, V.E. et al., "An Instrument for Transurethral Resection without Leakage of Current" Acta Medicotechnica vol. 24, No. 4, pp. 129-134, 1976.
Geddes, "Medical Device Accidents: With Illustrative Cases" CRC Press, 3 pgs, 1998.
Honig, W., "The Mechanism of Cutting in Electrosurgery" IEEE pp. 58-65, 1975.
Kramolowsky et al. "The Urological App of Electorsurgery" J. of Urology vol. 146, pp. 669-674, 1991.
Kramolowsky et al. "Use of 5F Bipolar Electrosurgical Probe in Endoscopic Urological Procedures" J. of Urology vol. 143, pp. 275-277, 1990.
Lee, B et al. "Thermal Compression and Molding of Artherosclerotic Vascular Tissue with Use" JACC vol. 13(5), pp. 1167-1171, 1989.
Letter from Department of Health to Jerry Malis dated Jan. 24, 1991, 3 pgs.
Letter from Department of Health to Jerry Malis dated Jul. 25, 1985, 1 pg.
Letter from Jerry Malis to FDA dated Jul. 25, 1985, 2 pgs.
Lu, et al., "Electrical Thermal Angioplasty: Catheter Design Features, In Vitro Tissue Ablation Studies and In Vitro Experimental Findings," Am J. Cardiol vol. 60, pp. 1117-1122, Nov. 1, 1987.
Malis, L., "Electrosurgery, Technical Note," J. Neursurg., vol. 85, pp. 970-975, Nov. 1996.
Malis, L., "Excerpted from a seminar by Leonard I. Malis, M.D. at the 1995 American Association of Neurological Surgeons Meeting," 1pg, 1995.
Malis, L., "Instrumentation for Microvascular Neurosurgery" Cerebrovascular Surgery, vol. 1, pp. 245-260, 1985.
Malis, L., "New Trends in Microsurgery and Applied Technology," Advanced Technology in Neurosurgery, pp. 1-16, 1988.
Malis, L., "The Value of Irrigation During Bipolar Coagulation" See ARTC 21602, 1 pg, Apr. 9, 1993.
Nardella, P.C., SPIE 1068: pp. 42-49, Radio Frequency Energy and Impedance Feedback, 1989.
O'Malley, Schaum's Outline of Theory and Problems of Basic Circuit Analysis, McGraw-Hill, $2^{nd}$ Ed., pp. 3-5, 1992.
Olsen MD, Bipolar Laparoscopic Cholecstectomy Lecture (marked confidential), 12 pgs, Oct. 7, 1991.
Pearce, John A. "Electrosurgery", pp. 17, 69-75, 87, John Wiley & Sons, New York, 1986.
Pearce, John A., "Electrosurgery", Handbook of Biomedical Engineering, chapter 3, Academic Press Inc., N. Y., pp. 98-113, 1988.
Piercey et al., "Electrosurgical Treatment of Experimental Bleeding Canine Gastric Ulcers" Gastroenterology vol. 74(3), pp. 527-534, 1978.
Protell et al., "Computer-Assisted Electrocoagulation: Bipolar v. Monopolar in the Treatment of Experimental Canine Gastric Ulcer Bleeding," Gastroenterology vol. 80, No. 3, pp. 451-455, 1981.
Ramsey et al., "A Comparison of Bipolar and Monopolar Diathermy Probes in Experimental Animals", Urological Research vol. 13, pp. 99-102, 1985.
Selikowitz et al., "Electric Current and Voltage Recordings on the Myocardium During Electrosurgical Procedures in Canines," Surgery, Gynecology & Obstetrics, vol. 164, pp. 219-224, Mar. 1987.
Shuman, "Bipolar Versus Monopolar Electrosurgery: Clinical Applications," Dentistry Today, vol. 20, No. 12, 7 pgs, Dec. 2001.
Slager et al. "Spark Erosion of Arteriosclerotic Plaques" Z. Kardiol. 76:Suppl. 6, pp. 67-71, 1987.
Slager et al. "Vaporization of Atherosclerotice Plaques by Spark Erosion" JACC 5(6): pp. 1382-1386, Jun. 1985.
Stoffels, E. et al., "Investigation on the Interaction Plasma-Bone Tissue", E-MRS Spring Meeting, 1 pg, Jun. 18-21, 2002.
Stoffels, E. et al., "Biomedical Applications of Plasmas", Tutorial presented prior to the $55^{th}$ Gaseous Electronics Conference in Minneapolis, MN, 41 pgs, Oct. 14, 2002.
Stoffels, E. et al., "Plasma Interactions with Living Cells", Eindhoven University of Technology, 1 pg, 2002.
Stoffels, E. et al., "Superficial Treatment of Mammalian Cells using Plasma Needle", J. Phys. D: Appl. Phys. 26, pp. 2908-2913, Nov. 19, 2003.
Stoffels, E. et al., "Plasma Needle", Eindhoven University of Technology, 1 pg, Nov. 28, 2003.
Stoffels, E. et al., "Plasma Physicists Move into Medicine", Physicsweb, 1 pg, Nov. 2003.
Stoffels, E. et al., "Plasma Treated Tissue Engineered Skin to Study Skin Damage", Biomechanics and Tissue Engineering, Materials Technology, 1 pg, 2003.

(56) References Cited

OTHER PUBLICATIONS

Stoffels, E. et al., "Plasma Treatment of Dental Cavities: A Feasibility Study", IEEE Transaction on Plasma Science, vol. 32, No. 4, pp. 1540-1542, Aug. 2004.
Stoffels, E. et al., "The Effects of UV Irradiation and Gas Plasma Treatment on Living Mammalian Cells and Bacteria: A Comparative Approach", IEEE Transaction on Plasma Science, vol. 32, No. 4, pp. 1544-1550, Aug. 2004.
Stoffels, E. et al., "Electrical and Optical Characterization of the Plasma Needle", New Journal of Physics 6, pp. 1-14, Oct. 28, 2004.
Stoffels, E. et al., "Where Plasma Meets Plasma", Eindhoven University of Technology, 23 pgs, 2004.
Stoffels, E. et al., "Gas Plasma effects on Living Cells", Physica Scripta, T107, pp. 79-82, 2004.
Stoffels, E. et al., "Plasma Treatment of Mammalian Vascular Cells: A Quantitative Description", IEEE Transaction on Plasma Science, vol. 33, No. 2, pp. 771-775, Apr. 2005.
Stoffels, E. et al., "Deactivation of *Escherichia Coli* by the Plasma Needle", J. Phys. D: Appl. Phys. 38, pp. 1716-1721, May 20, 2005.
Stoffels, E. et al., "Development of a Gas Plasma Catheter for Gas Plasma Surgery", XXVIIth ICPIG, Endoven University of Technology, pp. 18-22, Jul. 2005.
Stoffels, E. et al., "Development of a Smart Positioning Sensor for the Plasma Needle", Plasma Sources Sci. Technol. 15, pp. 582-589, Jun. 27, 2006.
Stoffels, E. et al., Killing of S. Mutans Bacteria Using a Plasma Needle at Atmospheric Pressure, IEEE Transaction on Plasma Science, vol. 34, No. 4, pp. 1317-1324, Aug. 2006.
Stoffels, E. et al., "Plasma-Needle Treatment of Substrates with Respect to Wettability and Growth of *Excherichia Coli* and *Streptococcus Mutans*", IEEE Transaction on Plasma Science, vol. 34, No. 4, pp. 1325-1330, Aug. 2006.
Stoffels, E. et al., "Reattachment and Apoptosis after Plasma-Needle Treatment of Cultured Cells", IEEE Transaction on Plasma Science, vol. 34, No. 4, pp. 1331-1336, Aug. 2006.
Stoffels, E. et al., "UV Excimer Lamp Irradiation of Fibroblasts: The Influence on Antioxidant Homostasis", IEEE Transaction on Plasma Science, vol. 34, No. 4, pp. 1359-1364, Aug. 2006.
Stoffels, E. et al., "Plasma Needle for in Vivo Medical Treatment: Recent Developments and Perspectives", Plasma Sources Sci. Technol. 15, pp. S169-S180, Oct. 6, 2006.
Swain, C.P., et al., "Which Electrode, A Comparison of four endoscopic methods of electrocoagulation in experimental bleeding ulcers" *Gut* vol. 25, pp. 1424-1431, 1987.
Tucker, R. et al., Abstract P14-11, p. 248, "A Bipolar Electrosurgical Turp Loop", Nov. 1989.
Tucker, R. et al. "A Comparison of Urologic Application of Bipolar Versus Monopolar Five French Electrosurgical Probes" *J. of Urology* vol. 141, pp. 662-665, 1989.
Tucker, R. et al. "In vivo effect of 5 French Bipolar and Monopolar Electrosurgical Probes on the Porcine Bladder" *Urological Research* vol. 18, pp. 291-294, 1990.
Tucker, R. et al., "Demodulated Low Frequency Currents from Electrosurgical Procedures," *Surgery, Gynecology and Obstetrics*, 159:39-43, 1984.
Tucker et al. "The interaction between electrosurgical generators, endoscopic electrodes, and tissue," Gastrointestinal Endoscopy, vol. 38, No. 2, pp. 118-122, 1992.
Valley Forge Scientific Corp., "Summary of Safety and Effective Information from 510K", 2pgs, 1991.
Valley Forge's New Products, CLINICA, 475, 5, Nov. 6, 1991.
Valleylab SSE2L Instruction Manual, 11 pgs, Jan. 6, 1983.
Valleylab, Inc. "Valleylab Part No. 945 100 102 A" Surgistat Service Manual, pp. 1-46, Jul. 1988.
Wattiez, Arnaud et al., "Electrosurgery in Operative Endoscopy," Electrosurgical Effects, Blackwell Science, pp. 85-93, 1995.
Wyeth, "Electrosurgical Unit" pp. 1181-1202, 2000.
Rand et al., "Effect of Elecctrocautery on Fresh Human Articular Cartilage", J. Arthro. Surg., vol. 1, pp. 242-246, 1985.
European Search Report for EP00123324.6 4 pgs, Mailed Jan. 16, 2001.
European Search Report for EP00928246 4 pgs, Mailed Mar. 7, 2008.
European Search Report for EP09153983 9 pgs, Mailed Apr. 1, 2009.
European Search Report for EP98964730.0 3 pgs, Mailed Nov. 20, 2000.
European Search Report for EP99922855.4 3 pgs, Aug. 2, 2001.
European Search Report for EP05762588 3 pgs, Apr. 12, 2010.
European Search Report for EP06760025.4 5 pgs, Nov. 10, 2010.
PCT International Preliminary Examination Report for PCT/US00/10674 4pgs, Mailed Mar. 7, 2001.
PCT International Preliminary Examination Report for PCT/US98/26624 4pgs, Mailed Oct. 12, 1999.
PCT International Preliminary Examination Report for PCT/US99/10062 3pgs, Jun. 20, 2000.
PCT International Preliminary Report on Patentability for PCT/US05/22373 4pgs, Dec. 28, 2006.
PCT International Preliminary Report on Patentability for PCT/US06/19095 6pgs, Nov. 20, 2007.
PCT International Search Report for PCT/US00/10674 1 pg, Mailed Jul. 27, 2000.
PCT International Search Report for PCT/US03/38782 1 pg, Mailed Jun. 30, 2004.
PCT International Search Report for PCT/US05/22373 1 pg, Mailed Oct. 3, 2006.
PCT International Search Report for PCT/US06/19095 2 pgs, Mailed Oct. 4, 2007.
PCT International Search Report for PCT/US96/08077 1 page, Mailed Sep. 16, 1996.
PCT International Search Report for PCT/US98/26624 1 page, Mailed Mar. 3, 1999.
PCT International Search Report for PCT/US99/10062 1 pg, Mailed Aug. 23, 1999.
UK Search Report for GB1111622.5 4pgs, Oct. 26, 2011.
UK Search Report for GB1202275.2 7pgs, May 11, 2012.

\* cited by examiner

SYSTEMS AND METHODS FOR TURBINATE REDUCTION

FIELD OF THE INVENTION

The present invention relates generally to the field of electrosurgery, and more particularly to surgical systems and methods which employ high frequency electrical energy to resect, reduce and treat target tissues, such as tissues within the nasal area. The present invention is particularly suited for turbinate reduction surgery and as a treatment for excessive nasal drainage or difficulty breathing.

BACKGROUND

Sinuses are the air-filled cavities insides the facial bones that open into the nasal cavities. Sinusitis is the inflammation of the mucous membranes of one or more of the paranasal sinus cavities. Sinusitis is often associated with a viral or bacterial upper respiratory infection that spreads to the sinuses. When the sinus opening becomes blocked, the cavities fill, producing deep pain and pressure. Postnasal or nasal drainage, nasal congestion with pressure, headaches, sinus infections and nasal polyps are most commonly associated with chronic sinusitis.

Treatment of mild sinusitis typically involves antibiotics, decongestants and analgesics, and is designed to prevent further complications. For more severe or chronic sinusitis, surgery is often necessary to return the nose and sinuses to normal function, particularly with patients who have undergone years of allergy treatment and still suffer from sinus blockage, or patients born with small sinuses and nasal passages. Recent developments in the field of endoscopic surgical techniques and medical devices have provided skilled physicians with instrumentation and methods to perform complicated paranasal sinus surgical procedures. Improved visualization of the nasal cavity and the paranasal sinuses, for example, has now made these anatomical areas more accessible to the endoscopic surgeon. As a result, functional endoscopic sinus surgery (FESS) has become the technique of choice in the surgical approach to sinus disease.

Another nasal symptom, runny noses (e.g., allergic rhinitis or vasomotor rhinitis), is typically caused by small shelf-like structures in the nose called turbinates. Turbinates are responsible for warming and humidifying the air passing through the nose into the lungs. When the air contains an irritant, the turbinates react to the airborne particles by swelling and pouring mucus, as if the body were trying to block and cleanse the breathing passage. For temporary relief of swollen turbinates, decongestant nasal sprays and pills are often prescribed. These measures, however, have limited effectiveness, and the long term use of such nasal sprays typically makes the problem worse. Moreover, decongestant pills may cause high blood pressure, increase the heart rate and, for some people, cause sleeplessness.

In the past several years, powered instrumentation, such as microdebrider devices and lasers, has been used to remove polyps or other swollen tissue in functional endoscopic sinus surgery. Microdebriders are disposable motorized cutters having a rotating shaft with a serrated distal tip for cutting and resecting tissue. The handle of the microdebrider is typically hollow, and it accommodates a small vacuum, which serves to aspirate debris. In this procedure, the distal tip of the shaft is endoscopically delivered through a nasal passage into the sinus cavity of a patient, and an endoscope is similarly delivered through the same or the opposite nasal passage to view the surgical site. An external motor rotates the shaft and the serrated tip, allowing the tip to cut the polyps or other tissue responsible for the sinus blockage. Once the critical blockage is cleared, aeration and drainage are reestablished and the sinuses heal and return to their normal function.

While microdebriders have been promising, these devices suffer from a number of disadvantages. For one, the tissue in the nasal and sinus cavities is extremely vascular, and the microdebrider severs blood vessels within this tissue, usually causing profuse bleeding that obstructs the surgeon's view of the target site. Controlling this bleeding can be difficult as the vacuuming action tends to promote hemorrhaging from blood vessels disrupted during the procedure. In addition, the microdebrider often must be removed from the nose periodically to cauterize severed blood vessels, which lengthens the procedure. Moreover, the serrated edges and other fine crevices of the microdebrider can easily become clogged with debris, which requires the surgeon to remove and clean the microdebrider during the surgery, further increasing the length of the procedure. More serious concerns, however, are that the microdebrider is not precise, and it is often difficult during the procedure to differentiate between the target sinus tissue and other structures within the nose, such as cartilage, bone or cranial. Thus, the surgeon must be extremely careful to minimize damage to the cartilage and bone within the nose, and to avoid damaging nerves, such as the optic nerve.

Lasers were initially considered ideal for sinus surgery because lasers ablate or vaporize tissue with heat, which also acts to cauterize and seal the small blood vessels in the tissue. Unfortunately, lasers are both expensive and somewhat tedious to use in these procedures. Another disadvantage with lasers is the difficulty in judging the depth of tissue ablation. Because the surgeon generally points and shoots the laser without contacting the tissue, he or she does not receive any tactile feedback to judge how deeply the laser is cutting. Healthy tissue, cartilage, bone and/or cranial nerves often lie within close proximity of the sinus tissue, making it is essential to maintain a minimum depth of tissue damage, which cannot always be ensured with a laser.

Treatments involving RF electrical energy based devices have previously been described, wherein the electrodes are predominantly disposed at the instrument tip, and are therefore limited in active size due to the small diameter of instrument required to access nasal passages. Such methods and apparatus are more fully described in previously filed applications, U.S. Pat. Nos. 6,053,172; 6,063,079; 6,659,106 and 7,442,191, the full disclosures of which have been incorporated by reference.

SUMMARY

The present disclosure presents an improved electrosurgical apparatus for treating tissue at a target site. The apparatus generally includes a shaft with a proximal end and a distal end portion and an active electrode and return electrode disposed on the distal end portion of the shaft. The apparatus may also have a plurality of apertures though the active electrode, operable to aspirate away any electrically conductive fluid, tissue and plasma by-products from the shaft distal end portion.

In one aspect an electrosurgical apparatus is disclosed for removing tissue from a body structure, this apparatus including a shaft having a proximal end and a distal portion; wherein the distal portion includes a return electrode and insulative electrode support. The return electrode may encircle the support and at least one active electrode may be disposed on the electrode support. This active electrode is oriented such that it has a proximal portion and a distal portion, and lies laterally on the shaft distal portion, with a plurality of aspiration apertures through the active electrode. These apertures are in fluid communication with a fluid aspiration cavity that is adjacent to the active electrode and within the electrode support. The aspiration cavity is also fluidly connected with a fluid aspiration element that is disposed within the shaft and the cavity and element together provide a conduit for the aspirated products to flow through and be removed from the treatment site.

The plurality of apertures varies in size and is organized so that the larger sized apertures are disposed towards the electrode proximal portion where suction is strongest. The stronger the suction, the larger the tissue fragments and plasma by-products may be successfully removed from the treatment site. The smaller sized apertures are disposed towards the electrode distal portion as this is where the suction is relatively weak and cannot readily remove the larger plasma by-products and fragments. This arrangement optimizes removal of the by-products and minimizes clogging of the fluid aspiration element. Additionally, at least one aspiration aperture may preferably have an axis of symmetry that is approximately coincident with or directly adjacent a long axis of the fluid aspiration cavity.

In another aspect an electrosurgical apparatus is disclosed for treating tissue at a target site, the apparatus having an elongate housing that has a handle end and a distal portion. On the distal portion is an electrode support, and this support is fluidly coupled to a first fluid conduit, the first fluid conduit located within the elongate housing. The electrode support also includes an aspiration cavity with a cavity ramp at one end. There is an active electrode on an electrode support shelf that is recessed within the electrode support and the active electrode has a number of apertures. The distal portion also includes a return electrode that encircles at least a portion of the electrode support. The plurality of apertures on the active electrode have at least a first plurality of apertures and a second plurality of apertures and the first plurality of apertures are sized larger than the second plurality of apertures All the apertures are fluidly coupled with the aspiration cavity and the second plurality of apertures are positioned over the cavity ramp.

In another aspect an electrosurgical apparatus is disclosed for removing tissue from a body structure, the apparatus including a shaft with a proximal end, a distal portion and a distal tip. The distal portion has a tubular insulating support member with at least one recessed support shelf that may support at least one active screen electrode. The active electrode may have at least one aperture. The support member may also have an aspiration cavity directly beneath the support shelf, so that fluid and plasma by-products may flow though the at least one aperture and into the aspiration cavity and then into a fluid aspiration element disposed along shaft. There may also be at least one flushing conduit disposed within the support member which is fluidly connected with a fluid supply element and the aspiration cavity, so that a fluid clear of any debris may be supplied to the distal portion via the supply element and a portion of this fluid may be flushed through the aspiration cavity and aspiration element to help maintain a clear suction path. This apparatus may also include a return electrode that encircles at least a portion of the tubular support member. The return electrode may also have at least one discharge aperture disposed through the return, which may also be fluidly connected with the fluid supply element. A portion of the fluid supply may then flow through at least one of these discharge apertures to wet to outer surface of the return electrode.

In yet another aspect an electrosurgical system is disclosed for treating tissue of a body structure. The system includes an electrosurgical controller, the electrosurgical controller configured to produce radio frequency (RF) energy at an active terminal with respect to a return terminal. The system also includes an electrosurgical wand coupled to the electrosurgical controller, the electrosurgical wand including an elongate shaft having a proximal end, a distal portion and a distal tip, with at least one active electrode disposed on the distal portion of the shaft, the at least one active electrode electrically coupled to the active terminal and a return electrode disposed on the distal portion of the shaft, the return electrode partially encircling the shaft distal portion and electrically coupled to the return terminal. Additionally there are a plurality of discharge apertures through the return electrode and fluidly connected to a fluid delivery element within shaft, the plurality of discharge apertures disposed on the opposing or inferior side relative to the at least one active electrode. The fluid delivery element may supply an electrically conductive fluid that flows through the discharge apertures and may wet the return electrode and improve the plasma formation. There may also be a plurality of aspiration apertures through the active electrode, which are variable in size. Adjacent the aspiration apertures is an aspiration cavity followed be an aspiration element, and together these both provide the conduit for the flow of aspirated products away from the target site. The larger aspiration apertures are disposed towards the proximal portion of the active electrode and the smaller aspiration apertures are disposed towards the distal portion of the active electrode.

In yet another aspect a method of performing a medical procedure on a body is disclosed. The method includes applying electrical energy between at least one active electrode and a return electrode in proximity to a conductive fluid; the active electrode and return electrode are disposed on an electrosurgical wand. Responsive to the energy, a plasma is then formed, proximate to the at least one active electrode. The active electrode is then rotated and translated to treat the tissue. The tissue and plasma by-products may then be aspirated through a plurality of aspiration apertures disposed through the active electrode and into an aspiration cavity, wherein at least one of the plurality of aspiration apertures has an axis of symmetry that is coincident with a longitudinal axis of the aspiration cavity. The smaller tissue and plasma by-products may be aspirated though at least one aspiration aperture that is disposed on the active electrode distal portion; and the larger sized tissue and plasma by-products may be aspirated through at least one larger sized aspiration aperture that is disposed on the active electrode proximal portion.

In yet another aspect a method of performing a medical procedure on a body is disclosed. The method includes flowing a conductive fluid within a fluid conduit disposed within an electrosurgical wand, so that the conductive fluid flows from a discharge aperture disposed through a return electrode and then flows around the return electrode so as to wet the return electrode surface, and flows toward an aspiration aperture disposed through an active electrode. Electrical energy is then applied between the active electrode and the return electrode, and responsive to the energy, a plasma is formed adjacent to the active electrode. A portion of a soft tissue within a body cavity is then removed by placing the active electrode within the body cavity, and translating the active electrode within the body cavity. Conductive fluid may be provided under pressure so as to expand the body cavity while removing the tissue, which may aid in forming a good plasma. The plasma may further emits a visible glow which may be observed either directly or through the body cavity walls, and the motion of the active electrode may be altered in response to the observed visible glow.

The present disclosure includes a number of important technical advantages. One technical advantage is that the lateral position of the electrodes allows for a relatively larger relative electrode surface area as compared to a minimal diameter instrument distal portion. Thereby, the surface area of the electrodes are not limited to the instrument diameter size compared with an instrument design having the electrodes limited to placement on the tip of the device only. Increased electrode surface area may contribute to the instrument and system being easier and quicker to use, as the treatment surface may then be relatively large, compared to instruments with the electrodes limited to the instrument tip. An additional technical advantage is the position of the lateral fluid delivery apertures, which allows for significant fluid delivery spread out over a broad surface area. This may optimize the return electrode "wetted" surface area by allowing for a more evenly and uniformly coated surface, creating a more uniform and even tissue effect.

An additional advantage is that the size of the wetted return surface area is not as limited compared with designs that locate the return on the instrument tip, allowing for a larger treatment surface and larger, more optimum surface area ratios between the active electrode and return. Another advantage is that the return may partially encircle the active electrode without adding significantly to the instrument diameter, compared with instruments with the electrodes limited to the instrument tip where the return electrode must be spaced proximally away from the active electrode. Additionally, configuring the return electrode to partially encircle the active electrode may improve the uniformity of the tissue effect. An additional advantage is that the suction apertures are less limited in size or number, potentially allowing for more suction apertures than a design that limits the suction apertures to the instrument tip, thereby creating better aspiration and improving the surgeon's ability to view the surgical site. An additional advantage is that the suction is optimized such that the likelihood of clogging is reduced due to the arrangement of aspiration apertures and flushing conduit. Additional advantages will be apparent to those of skill in the art and from the figures, description and claims provided herein.

BRIEF DESCRIPTION OF THE DRAWINGS

The invention may best be understood by reference to the following description taken in conjunction with the accompanying drawings in which.

DETAILED DESCRIPTION

Before the present invention is described in detail, it is to be understood that this invention is not limited to particular variations set forth herein as various changes or modifications may be made to the invention described and equivalents may be substituted without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Last, it is to be appreciated that unless defined otherwise, all technical and scientific terms used herein have the same meaning as commonly understood by one of ordinary skill in the art to which this invention belongs.

Figure 1:
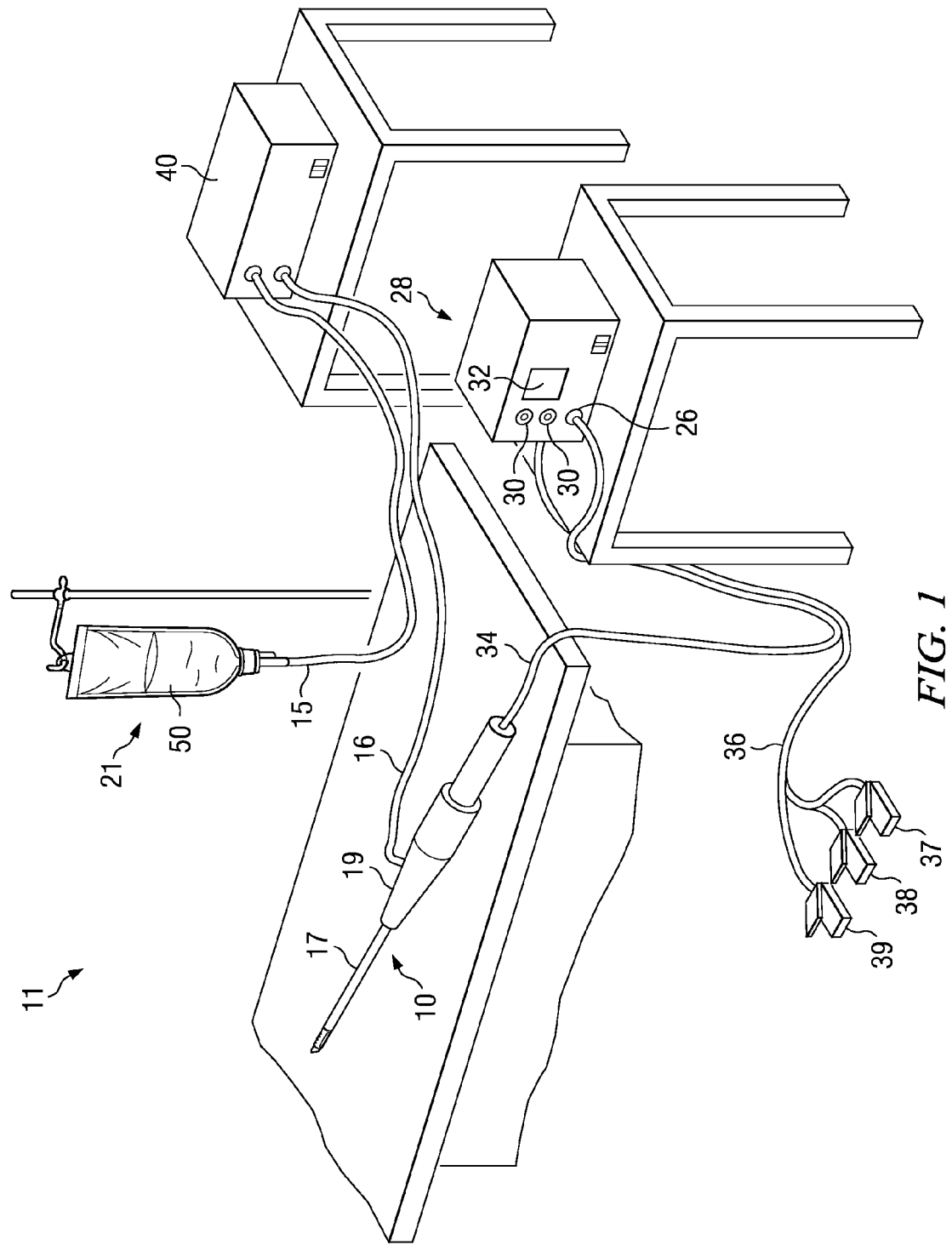
FIG. 1 shows a perspective view of an electrosurgical system according to at least certain embodiments.

Referring to FIG. 1, an exemplary electrosurgical system 11 for treatment of tissue in accordance with the present disclosure will now be described in detail. Electrosurgical system 11 generally comprises electrosurgical handpiece, instrument, apparatus or probe 10 electrically connected to an electrosurgical controller (i.e., power supply) 28 for providing high frequency voltage to a target site; and a fluid source 21 for supplying electrically conducting fluid 50 to probe 10 via fluid delivery tube 15. Fluid delivery may be controlled by pump 40, to provide a variable fluid flow supply to probe 10 via delivery tube 16. In addition, electrosurgical system 11 may include an endoscope (not shown) with a fiber optic head light for viewing the surgical site, particularly in sinus procedures or procedures in the ear or the back of the mouth. The endoscope may be integral with probe 10, or it may be part of a separate instrument. The system 11 may also include a vacuum source (not shown) for coupling to a suction or aspiration lumen or tube (not shown) in the probe 10 for aspirating the target site.

Exemplary electrosurgical probe 10 comprises a handle 19 and an elongate shaft 17 extending from handle 19. The proximal and distal portions of handle 19 typically comprise a plastic material that is easily molded into a suitable shape for handling by the surgeon. As shown, a connecting cable 34 has a connector 26 for electrically coupling the active electrode and return electrode (described in more detail in later figures) on probe 10 to power supply 28. Power supply 28 has an operator controllable voltage level adjustment 30 to change the applied voltage level, which is observable at a voltage level display 32. Power supply 28 may also include first, second and third foot pedals 37, 38, 39 and a cable 36 which is removably coupled to power supply 28. The foot pedals 37, 38, 39 allow the surgeon to remotely adjust the energy level applied to active electrode 58. In an exemplary embodiment, first foot pedal 37 is used to place the power supply into the "ablation" mode and second foot pedal 38 places power supply 28 into a "subablation" mode (i.e., contraction, coagulation or other types of tissue modification without volumetric tissue removal). The third foot pedal 39 (or in some embodiments a foot-activated button) allows the user to adjust the voltage level within the "ablation" mode.

The electrosurgical system 11 of the various embodiments may have a variety of operational modes. One such mode employs Coblation® technology. The assignee of the present invention developed Coblation® technology. Coblation® technology involves the application of a high frequency voltage difference between one or more active electrode(s) and one or more return electrode(s) of the wand 10 to develop high electric field intensities in the vicinity of the target tissue. The high electric field intensities may be generated by applying a high frequency voltage that is sufficient to vaporize an electrically conductive fluid over at least a portion of the active electrode(s) in the region between the tip of the active electrode(s) and the target tissue. The electrically conductive fluid may be a liquid or gas, such as isotonic saline, blood, extracelluar or intracellular fluid, delivered to, or already present at, the target site, or a viscous fluid, such as a gel, applied to the target site.

When the conductive fluid is heated enough such that atoms vaporize off the surface faster than they recondense, a gas is formed. When the gas is sufficiently heated such that the atoms collide with each other causing a release of electrons in the process, an ionized gas or plasma is formed (the so-called "fourth state of matter"). Generally speaking, plasmas may be formed by heating a gas and ionizing the gas by driving an electric current through it, or by shining radio waves into the gas. These methods of plasma formation give energy to free electrons in the plasma directly, and then electron-atom collisions liberate more electrons, and the process cascades until the desired degree of ionization is achieved. Additionally, the ionization of atoms within the vapor layer produced in isotonic saline, (containing sodium chloride) leads to the generation of energetic photons having wavelengths, by way of example, in the range of 306 to 315 nanometers (ultraviolet spectrum) and 588-590 nanometers (visible spectrum).

In the case of the plasma formed by Coblation® technology, the electric field across the vapor layer generates high energy electrons that break down the water molecules into energized radicals, some of which are extremely chemically active. The vapor layer then becomes a low temperature gas, containing highly energized particles, otherwise known as "glow discharge plasma" or "non-equilibrium plasma." Non-equilibrium plasma is a low temperature gas in which each of the excited particles emits a specific light. When the active electrodes of wand 10 are submerged in isotonic saline, the electrical discharges produce strong optical emissions typically from the dominant sodium D-lines which are responsible for a characteristic yellow to orange glow at the active electrode indicating the presence of plasma. A more complete description of plasma can be found in Plasma Physics, by R. J. Goldston and P. H. Rutherford of the Plasma Physics Laboratory of Princeton University (1995), the complete disclosure of which is incorporated herein by reference.

As the density of the plasma or vapor layer becomes sufficiently low (i.e., less than approximately 1020 atoms/cm3 for aqueous solutions), the electron mean free path increases to enable subsequently injected electrons to cause impact ionization within the vapor layer. Once the ionic particles in the plasma layer have sufficient energy, they accelerate towards the target tissue. Energy evolved by the energetic electrons (e.g., 3.5 eV to 5 eV) can subsequently bombard a molecule and break its bonds, dissociating a molecule into free radicals, which then combine into final gaseous or liquid species. Often, the electrons carry the electrical current or absorb the radio waves and, therefore, are hotter than the ions. Thus, the electrons, which are carried away from the tissue towards the return electrode, carry most of the plasma's heat with them, allowing the ions to break apart the tissue molecules in a substantially non-thermal manner.

By means of this molecular dissociation (rather than thermal evaporation or carbonization), the target tissue structure is volumetrically removed through molecular disintegration of larger organic molecules into smaller molecules and/or atoms, such as hydrogen, oxygen, oxides of carbon, hydrocarbons and nitrogen compounds. This molecular disintegration completely removes the tissue structure, as opposed to dehydrating the tissue material by the removal of liquid within the cells of the tissue and extracellular fluids, as is typically the case with electrosurgical desiccation and vaporization. A more detailed description of this phenomena can be found in commonly assigned U.S. Pat. No. 5,697,882, the complete disclosure of which is incorporated herein by reference.

In some applications of the Coblation® technology, high frequency (RF) electrical energy is applied in an electrically conducting media environment to shrink or remove (i.e., resect, cut, or ablate) a tissue structure and to seal transected vessels within the region of the target tissue. Coblation® technology is also useful for sealing larger arterial vessels, e.g., on the order of about 1 mm in diameter. In such applications, a high frequency power supply is provided having an ablation mode, wherein a first voltage is applied to an active electrode sufficient to effect molecular dissociation or disintegration of the tissue, and a coagulation mode, wherein a second, lower voltage is applied to an active electrode (either the same or a different electrode) sufficient to heat, shrink, and/or achieve hemostasis of severed vessels within the tissue.

The amount of energy produced by the Coblation® device may be varied by adjusting a variety of factors, such as: the number of active electrodes; electrode size and spacing; electrode surface area; asperities and sharp edges on the electrode surfaces; electrode materials; applied voltage and power; current limiting means, such as inductors; electrical conductivity of the fluid in contact with the electrodes; density of the fluid; and other factors. Accordingly, these factors can be manipulated to control the energy level of the excited electrons. Since different tissue structures have different molecular bonds, the Coblation® device may be configured to produce energy sufficient to break the molecular bonds of certain tissue but insufficient to break the molecular bonds of other tissue. For example, fatty tissue (e.g., adipose) has double bonds that require an energy level substantially higher than 4 eV to 5 eV (typically on the order of about 8 eV) to break. Accordingly, the Coblation® technology generally does not ablate or remove such fatty tissue; however, it may be used to effectively ablate cells to release the inner fat content in a liquid form. Of course, factors may be changed such that these double bonds can also be broken in a similar fashion as the single bonds (e.g., increasing voltage or changing the electrode configuration to increase the current density at the electrode tips). A more complete description of this phenomenon can be found in commonly assigned U.S. Pat. Nos. 6,355,032; 6,149,120 and 6,296,136, the complete disclosures of which are incorporated herein by reference.

The active electrode(s) of a Coblation® device may be supported within or by an inorganic insulating support positioned near the distal end of the instrument shaft. The return electrode may be located on the instrument shaft, on another instrument or on the external surface of the patient (i.e., a dispersive pad). The proximal end of the instrument(s) will include the appropriate electrical connections for coupling the return electrode(s) and the active electrode(s) to a high frequency power supply, such as an electrosurgical generator.

In one example of a Coblation® device for use with the present invention, the return electrode of the device is typically spaced proximally from the active electrode(s) a suitable distance to avoid electrical shorting between the active and return electrodes in the presence of electrically conductive fluid. In many cases, the distal edge of the exposed surface of the return electrode is spaced about 0.5 mm to 25 mm from the proximal edge of the exposed surface of the active electrode(s). Of course, this distance may vary with different voltage ranges, conductive fluids, and depending on the proximity of tissue structures to active and return electrodes. The return electrode will typically have an exposed length in the range of about 1 mm to 20 mm.

The voltage difference applied between the return electrode(s) and the active electrode(s) will be at high or radio frequency, typically between about 5 kHz and 20 MHz, usually being between about 30 kHz and 2.5 MHz, preferably being between about 50 kHz and 500 kHz, often less than 350 kHz, and often between about 100 kHz and 200 kHz. In some applications, applicant has found that a frequency of about 100 kHz is useful because the tissue impedance is much greater at this frequency. In other applications, such as procedures in or around the heart or head and neck, higher frequencies may be desirable (e.g., 400-600 kHz) to minimize low frequency current flow into the heart or the nerves of the head and neck.

The RMS (root mean square) voltage applied will usually be in the range from about 5 volts to 1000 volts, preferably being in the range from about 10 volts to 500 volts, often between about 150 volts to 400 volts depending on the active electrode size, the operating frequency and the operation mode of the particular procedure or desired effect on the tissue (i.e., contraction, coagulation, cutting or ablation.)

Typically, the peak-to-peak voltage for ablation or cutting with a square wave form will be in the range of 10 volts to 2000 volts and preferably in the range of 100 volts to 1800 volts and more preferably in the range of about 300 volts to 1500 volts, often in the range of about 300 volts to 800 volts peak to peak (again, depending on the electrode size, number of electrodes, the operating frequency and the operation mode). Lower peak-to-peak voltages will be used for tissue coagulation, thermal heating of tissue, or collagen contraction and will typically be in the range from 50 to 1500, preferably 100 to 1000 and more preferably 120 to 400 volts peak-to-peak (again, these values are computed using a square wave form). Higher peak-to-peak voltages, e.g., greater than about 800 volts peak-to-peak, may be desirable for ablation of harder material, such as bone, depending on other factors, such as the electrode geometries and the composition of the conductive fluid.

As discussed above, the voltage is usually delivered in a series of voltage pulses or alternating current of time varying voltage amplitude with a sufficiently high frequency (e.g., on the order of 5 kHz to 20 MHz) such that the voltage is effectively applied continuously (as compared with, e.g., lasers claiming small depths of necrosis, which are generally pulsed about 10 Hz to 20 Hz). In addition, the duty cycle (i.e., cumulative time in any one-second interval that energy is applied) is on the order of about 50% for the present invention, as compared with pulsed lasers which typically have a duty cycle of about 0.0001%.

The preferred power source of the present invention delivers a high frequency current selectable to generate average power levels ranging from several milliwatts to tens of watts per electrode, depending on the volume of target tissue being treated, and/or the maximum allowed temperature selected for the instrument tip. The power source allows the user to select the voltage level according to the specific requirements of a particular neurosurgery procedure, cardiac surgery, arthroscopic surgery, dermatological procedure, ophthalmic procedures, open surgery or other endoscopic surgery procedure. For cardiac procedures and potentially for neurosurgery, the power source may have an additional filter, for filtering leakage voltages at frequencies below 100 kHz, particularly voltages around 60 kHz. Alternatively, a power source having a higher operating frequency, e.g., 300 kHz to 600 kHz may be used in certain procedures in which stray low frequency currents may be problematic. A description of one suitable power source can be found in commonly assigned U.S. Pat. Nos. 6,142,992 and 6,235,020, the complete disclosure of both patents are incorporated herein by reference for all purposes.

The power source may be current limited or otherwise controlled so that undesired heating of the target tissue or surrounding (non-target) tissue does not occur. In a presently preferred embodiment of the present invention, current limiting inductors are placed in series with each independent active electrode, where the inductance of the inductor is in the range of 10 uH to 50,000 uH, depending on the electrical properties of the target tissue, the desired tissue heating rate and the operating frequency.

Alternatively, capacitor-inductor (LC) circuit structures may be employed, as described previously in U.S. Pat. No. 5,697,909, the complete disclosure of which is incorporated herein by reference. Additionally, current-limiting resistors may be selected. Preferably, these resistors will have a large positive temperature coefficient of resistance so that, as the current level begins to rise for any individual active electrode in contact with a low resistance medium (e.g., saline irrigant or blood), the resistance of the current limiting resistor increases significantly, thereby minimizing the power delivery from said active electrode into the low resistance medium (e.g., saline irrigant or blood).

In the Coblation mode, a sufficient voltage is applied to the electrode terminals to establish the requisite conditions for molecular dissociation of the tissue (i.e., vaporizing a portion of the electrically conductive fluid, ionizing charged particles within the vapor layer and accelerating these charged particles against the tissue). As discussed above, the requisite voltage level for ablation will vary depending on the number, size, shape and spacing of the electrodes, the distance in which the electrodes extend from the support member, etc. Once the surgeon places the power supply in the "ablation" modes, voltage level adjustment 30 or third foot pedal 39 may be used to adjust the voltage level to adjust the degree or aggressiveness of the ablation.

Of course, it will be recognized that the voltage and modality of the power supply may be controlled by other input devices, by a variety of switches or toggles placed on the handle 19 for example. However, applicant has found that foot pedals are convenient methods of controlling the power supply while manipulating the probe during a surgical procedure.

In the subablation (or coagulation) mode, the power supply 28 applies a sufficiently low voltage to the active electrode to avoid vaporization of the electrically conductive fluid and subsequent molecular dissociation of the tissue. The surgeon may automatically toggle the power supply between the ablation and subablation modes by alternatively stepping on foot pedals 37, 38, respectively. This allows, for example, the surgeon to quickly move between coagulation and ablation in situ, without having to remove his/her concentration from the surgical field or without having to request an assistant to switch the power supply. By way of example, as the surgeon sculpts soft tissue in the ablation mode, the probe typically will simultaneously seal and/or coagulation small severed vessels within the tissue. However, larger vessels, or vessels with high fluid pressures (e.g., arterial vessels) may not be sealed in the ablation mode. Accordingly, the surgeon can simply step on foot pedal 38, automatically lowering the voltage level below the threshold level for ablation, and apply sufficient pressure onto the severed vessel for a sufficient period of time to seal and/or coagulate the vessel. After this is completed, the surgeon may quickly move back into the ablation mode by stepping on foot pedal 37.

Figure 2A:
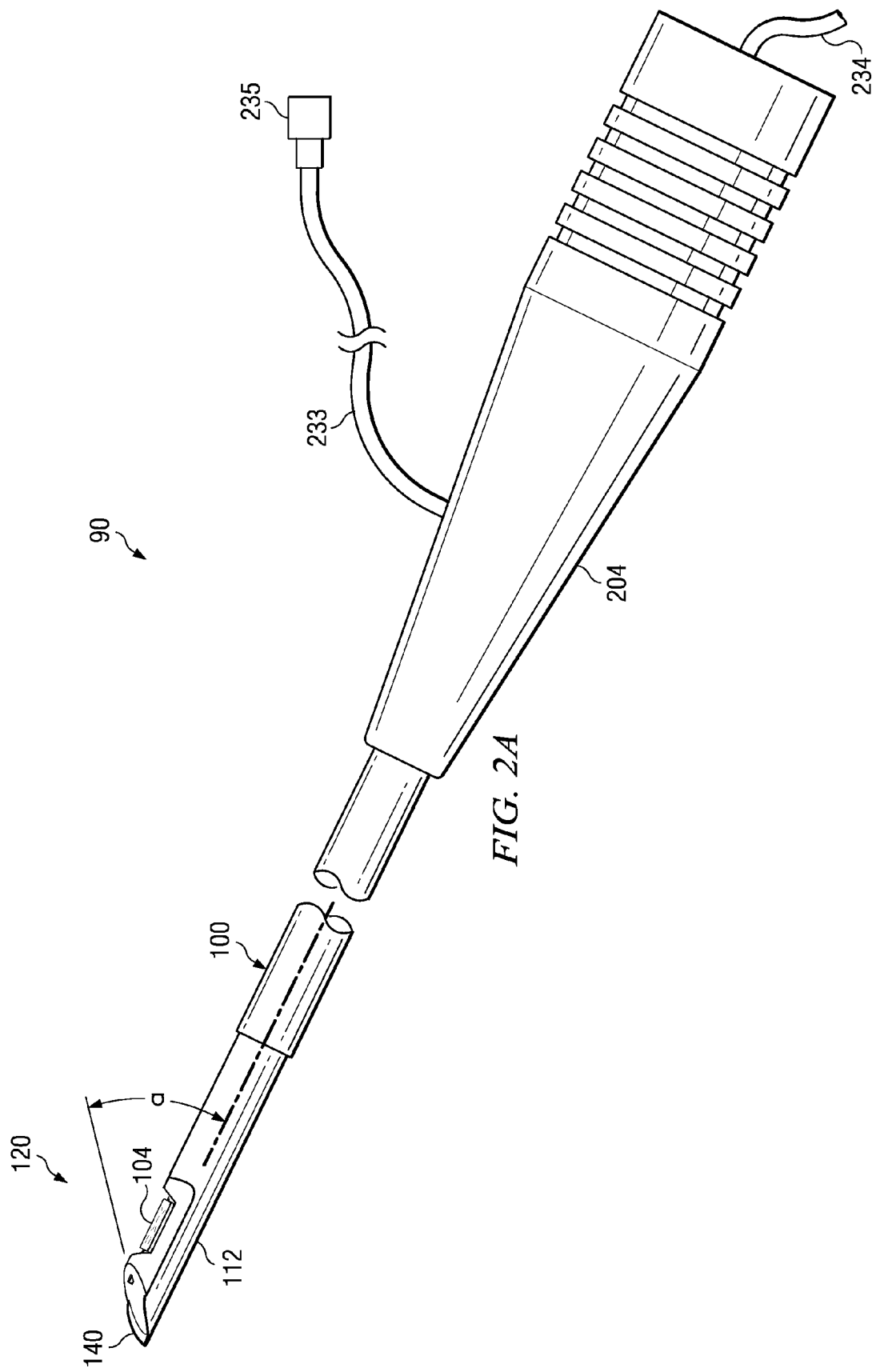
FIG. 2A shows an apparatus for treating tissue according to at least certain embodiments.

FIG. 2A illustrates an exemplary electrosurgical instrument 90 constructed according to the principles of the present disclosure. As shown in FIG. 2A, probe 90 generally includes an elongate shaft 100 which may be flexible or rigid, and a handle 204 coupled to the proximal end of shaft 100. Shaft 100 may include a bend or curve (not shown) that may allow the distal portion 120 of shaft 100 to be offset or at a different angle from the shaft proximal section and handle 204. This offset may facilitate procedures that require an endoscope, because the endoscope can, for example, be introduced through the same nasal passage as the shaft 100 without interference between handle 204 and the eyepiece of the endoscope. In alternative embodiments, shaft 100 may be malleable so that the surgeon may create the curve or bend that is preferred for the specific patient or endoscopic needs.

Handle 204 typically comprises a plastic material that is easily molded into a suitable shape for handling by the surgeon. Handle 204 defines an inner cavity (not shown) that houses the electrical connections (not shown) and provides a suitable interface for connection to an electrical connecting cable 234. As shown in FIG. 2A, a fluid tube or inlet 233 extends through an opening in handle 204, and may include a connector 235 for connection to a fluid supply source and fluid supply pump (described earlier), for supplying electrically conductive fluid to the instrument distal portion 120 and subsequently to the target site. Depending on the configuration of the distal surface of shaft 100, fluid tube 233 may extend through a single lumen (not shown) within shaft 100, or the tube 233 may fluidly connect with a fluid supply conduit disposed within the shaft 100 (described in more detail later), or tube 233 may be coupled to a plurality of lumens (not shown) that extend through shaft 100. In alternative embodiments, fluid tube 233 may extend along the exterior of shaft 100 to a point just proximal of distal portion 120. Probe 90 may also include a valve or equivalent structure (not shown) located on the instrument 90 or tubing 233, for controlling the flow rate of the electrically conducting fluid to the target site.

In certain embodiments, the distal portion of shaft 100 comprises a flexible material which may be deflected relative to the longitudinal axis of the shaft 100. Such deflection may be selectively induced by mechanical tension of a pull wire, for example, or by a shape memory wire that expands or contracts by externally applied temperature changes. A bend in the distal portion of shaft 100 is particularly advantageous in the treatment of sinus tissue as it allows the surgeon to reach the target tissue within the nose as the shaft 100 extends through the nasal passage. Of course, it will be recognized that the shaft may have different angles depending on the procedure. For example, a shaft having a 90° bend angle may be particularly useful for accessing tissue located in the back portion of the mouth and a shaft having a 10° to 30° bend angle may be useful for accessing tissue near or in the front portion of the mouth or nose.

In the embodiment shown in FIGS. 2A, probe 90 generally includes a shaft distal portion 120 and distal tip 140. Distal tip 140 may not be energized but may include a leading sharp, jagged or piercing edge, operable to help gain access, dissect tissue or create a window into tissue such as a polyp or turbinate. Distal tip 140 may be rigid; enabling it to be more readily directed into a targeted body structure and thereby provide access to the inside of the body structure. In this embodiment, distal tip 140 may be the distal tip of shaft 100 and may be energized or part of the return electrode 112 (described later). Distal tip 140 may be oriented at an angle α to the long axis of the shaft 100, so as to ease insertion of the tip 140 into tissue, with the angle being approximately 40 degrees relative to shaft long axis.

Distal portion 120 includes at least one return electrode 112 and at least one active electrode 104. As shown in more detail in FIG. 2B, return electrode 112 encircles at least a portion of the shaft distal portion 120 and may extend distally and proximally relative to the active electrode 104 so that the active electrode 104 is generally surrounded or at least partially encircled. Return electrode 112 may be approximately tubular shaped and extend along shaft 100. Return electrode 112 is shown with an opening, channel or slot, so as to expose a portion of electrode support 150 and in order to position portions of return electrode 112 adjacent active electrode 104. As shown here, a portion of the return electrode 112 is disposed on the approximate opposing side or inferior side or surface of the shaft relative to the active electrode 104. The return electrode 112 is preferably disposed in such a way as to maintain a substantially uniform gap or dimension 106 between the closest point on the active electrode 104 to the adjacent return electrode opening edge 114 surrounding the active electrode, for as much of the active electrode 104 profile as possible.

Figure 2B:
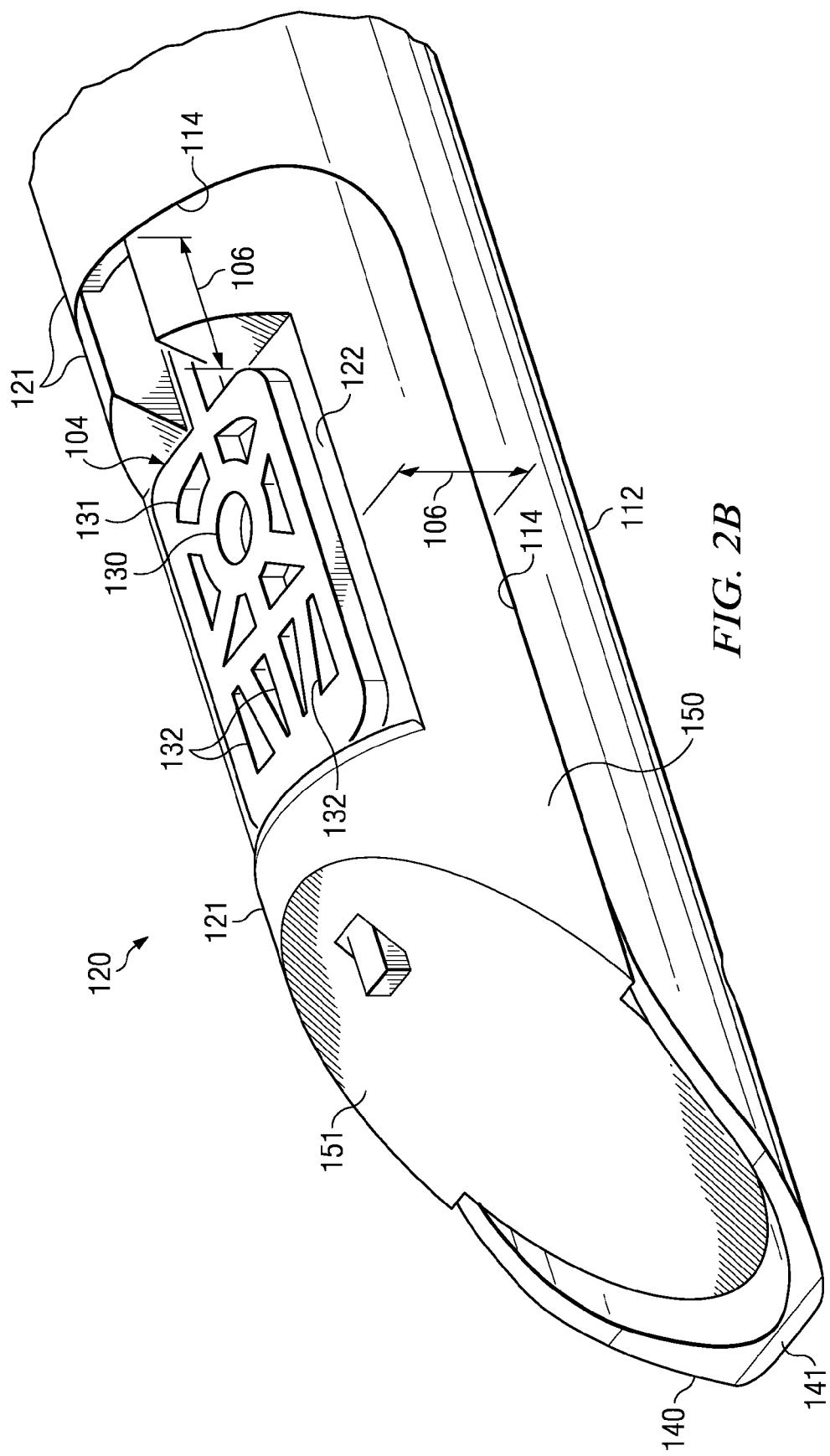
FIG. 2B shows an instrument shaft distal end portion, according to at least certain embodiments.

In the embodiment shown in FIG. 2B, the return electrode 112 partially encircles the active electrode 104 on the proximal side of the active electrode 104 and a portion of the lateral sides of the active electrode 104. By maintaining a substantially consistent distance along a significant portion of the length of the opening edge, this configuration of the return electrode 112 shown in FIG. 2B is believed to maintain a more uniform tissue effect along the proximal and proximal portions of the lateral sides of the active electrode 104. In addition, the smaller the dimension 106, the lower the energy or voltage that may be required by a power supply to create a required tissue effect, and the more localized the tissue effect may be, creating a very controlled tissue effect, which is preferable to the surgeon. This may minimize unwanted tissue treatment outside the intended area. In the embodiment shown, dimension 106 may be between approximately 0.2 mm and 3 mm, and for certain embodiments may preferably be approximately 0.8 mm.

Active electrode 104 is disposed on a support shelf 122 on electrode support 150, and this support shelf 122 is oriented approximately parallel to the longitudinal axis of the shaft distal portion 120 and recessed from or offset from the superior surface 121 of the shaft distal portion 120. Active electrode 104 may comprise a screen electrode or substantially flat electrode, with the flat surface at least partially supported by support shelf 122. Active electrode 104 is recessed or offset from shaft superior surface 121 to form a gap or space between the superior surface of the active electrode 104 and a target tissue, especially when distal portion 120 is inserted within a body cavity for treatment. Having the tissue somewhat spaced away from electrode 104 may allow for adequate wetting of active electrode 104, creating optimal conditions for plasma formation, as described earlier. Active electrode 104 has a thickness, with a number of apertures 130, 131 and 132 of varying sizes, disposed through the thickness. Conductive fluid together with tissue fragments and plasma by-products may then be removed from the area adjacent the active electrode 104 via electrode apertures 130, 131 and 132 into a suction cavity 135 or aspiration cavity (shown in more detail in FIGS. 2C and 2E) disposed within electrode support 150 and below or on the inferior side of the active electrode 104. The tissue fragments and plasma by-products may then flow from this cavity 135 into and along an aspiration element (described later) disposed within shaft 100 (not shown here) that is fluidly connected with the aspiration cavity 135. The shelf 122 preferably recesses the electrode 104 away slightly from the target tissue to allow for optimal flow of these fragments and ablation by-products away from a treated tissue surface and then into and through apertures 130, 131 and 132.

At least a first set or plurality of active electrode aspiration apertures 130 and 131 are disposed towards the proximal portion of active electrode 104 and are preferably larger than a second set or plurality of aspiration apertures 132 disposed on a distal portion of active electrode 104. Additionally, with regard to aperture 130 in particular, in certain embodiments it is preferred that the axis of symmetry of the largest aspiration aperture is positioned to align with a longitudinal axis of cavity 135 (i.e., the largest aperture is centered relative to cavity 135). This arrangement of varying sized aspiration apertures is to optimize aspiration without concurrent clogging of either the apertures or the aspiration cavity 135. The realized suction pressure is generally stronger along the longitudinal axis of the aspiration cavity and at the proximal end of the cavity and active electrode 104 as compared with that at the distal end of active electrode 104 and aspiration cavity 135. Larger fragments and by-products may then pass through these larger, first plurality of apertures 130 and 131, and then be successfully removed and transported out of suction cavity 135 and through suction element by the stronger suction. Should these larger fragments be allowed to enter the suction cavity 135 at the distal end of the active electrode 104 and the distal portion of the suction cavity 135 where suction is relatively weaker, the fragments have a higher likelihood of collecting in the cavity 135 and promoting clogging of the aspiration element. More particularly, the occurrence of larger fragments gathering in a more distal area of cavity 135 where suction pressure is relatively lower may contribute to multiple larger fragments collecting together, and potentially forming even larger fragments or an increased density of fragments, and increasing the likelihood of clogging the suction cavity 135 and/or element.

As previously described, the largest aperture 130 or maximum aperture 130 may be positioned to align with the longitudinal axis of aspiration cavity 135 for optimum tissue and ablation by-products removal through this aperture 130. Additionally it is preferable that, should the maximum aperture 130 be asymmetrical, the aperture 130 should be oriented such that the axis of symmetry with the greatest dimension should align with or be coincident with the longitudinal axis of the aspiration cavity 135 (i.e., in the case of an oval shaped maximum aperture 130, the axis of symmetry with the greatest dimension should align with the cavity long axis). Therefore, in order to optimize aspiration capabilities, at least one larger aperture is preferably positioned both toward the proximal portion of the active electrode 104, as well as particularly aligning the aperture's axis of symmetry with the greatest dimension with the longitudinal axis of the aspiration cavity 135.

Apertures 130, 131 and 132 all generally have sharp edges, so as to promote plasma formation at these locations necessary to digest tissue fragments as they flow through the apertures 130, 131 and 132. Tissue fragments and plasma by-products are generally removed from the treatment site by travelling though one of said apertures 130, 131 or 132 and may clog the suction element (not shown here). Apertures 130, 131 and 132 with multiple edge surfaces may preferably promote plasma formation at these locations in order to further digest or reduce in size any tissue fragments or plasma by-products travelling through apertures 130, 131 or 132, and thereby reduce the likelihood of clogging. Additionally, any diameter or cross-sectional dimension of the fluid aspiration element is preferably larger than that of any of the apertures 130, 131 or 132, to minimize clogging of the aspiration element.

As described earlier, instrument tip 140 is generally smooth and angled to provide good access to target tissue. The distal leading edge 141 may be sharp so as to cut through tissue to gain access to the target tissue. Distal edge 141 may be electrically connected with the return electrode 112 or may comprise a distal most portion of return electrode 112, as shown in this embodiment and may use RF electrical energy to help break though tissue and create hemostasis. The distal portion of electrode support 150 comprises an angled plane 151 that makes up a portion of tip 140, and the plane 151 may be offset proximally from distal edge 141 and approximately parallel to the angle of distal edge 141. As shown in FIG. 2B, the distal portion of return electrode 112 and distal portion of electrode support member 150 is preferably formed so that the electrode support 150 nests within return electrode 112 and they generally fit together smoothly with minimal jagged edges so as to minimize any snagging on tissue during instrument insertion. In this configuration, return electrode 112 encircles a portion of support member 150.

Figure 2C:
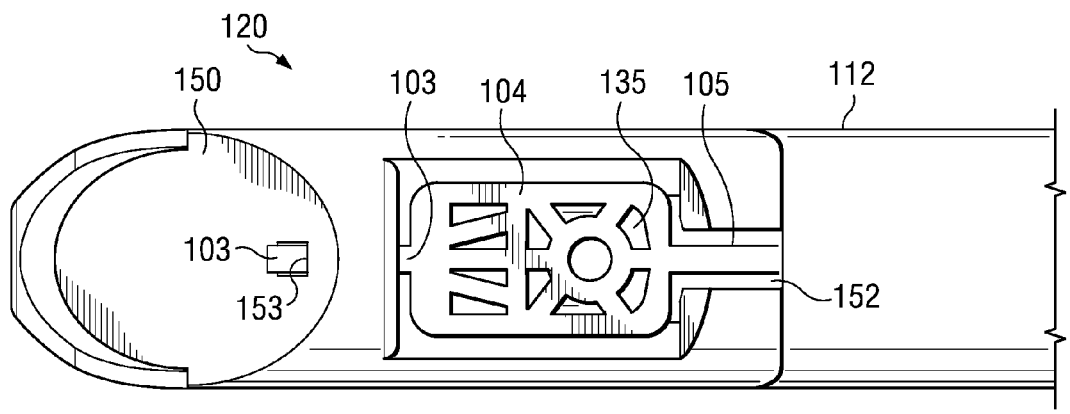
FIG. 2C shows a superior view of an instrument distal end portion according to at least certain embodiments.

Now referring to FIG. 2C, a superior view of shaft distal portion 120 is shown. Electrode 104 is preferably connected to the power supply (described earlier) via a proximally extending electrode leg 105, that may extend from the proximal end of electrode 104 proximally toward the handle where it may connect with other electrically conducting means that electrically couple with the power supply. Electrode leg 105 is approximately the same thickness as active electrode 104 to ease manufacture and lies within a channeled portion 152 of support 150. Leg 105 may press fit within channel 152 and then be further fixed into position using mechanical fixing means such as adhesive or sealant within channel 152. Electrode 104 may also comprise a distal leg 103 that extends distally from the electrode 104 and through a distal support opening 153 in support member 150. Distal leg 103 is primarily used to stabilize and fix the electrode 104 in position. Distal leg 103 may be press fit or snap fit into opening 153 or mechanically fixed using an adhesive or sealant. Both proximal and distal legs 105 and 103 are shown disposed along the central axis of electrode 104 and approximately parallel and in line with each other. FIG. 2C shows the distal leg protruding distally from tunnel 153 and may provide some tissue effect should it contact tissue. In alternative embodiments, not shown here, distal leg 103 may be recessed within tunnel 153 and therefore spaced away from any tissue. Active electrode 104 together with proximal leg 105 and distal leg 103, may be formed from one sheet of electrically conductive material, and may preferably formed using laser cutting, MIM or an EDM process to form the legs as well as the electrode and aperture (130, 131 and 132) shapes.

Figure 2D:
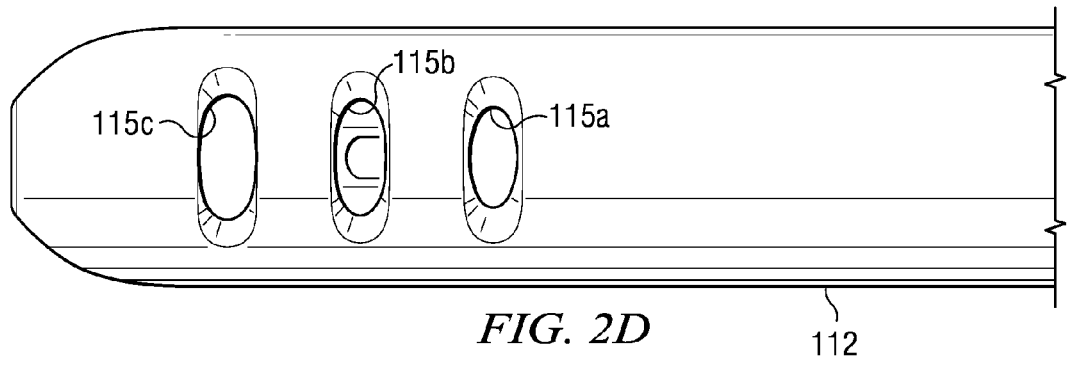
FIG. 2D shows an inferior view of an instrument distal end portion according to at least certain embodiments.

Return electrode 112 is spaced away from and not directly connected to active electrode 104. To complete the current path so that an electrical current may flow between active electrode 104 and return electrode 112, electrically conducting fluid (e.g., isotonic saline) is caused to be present and flow there between. Referring now to FIG. 2D, in order to supply fluid, return electrode 112 includes at least one discharge aperture formed through the return electrode 112. Three discharge apertures 115a, 115b and 115c are shown, each disposed axially relative to each other with their center aligned with each other as well as the longitudinal axis of shaft 100. At least one discharge aperture is oriented in a generally radial direction with respect to shaft 100 and on the inferior side of shaft distal end portion 120 (i.e., on the opposing side of the shaft from active electrode 104). Fluid is preferably discharged from discharge apertures 115a, 115b and 115c to wet the return electrode 112 and then flow circumferentially around distal end portion 120 towards active electrode 104. In the shown embodiment, multiple apertures 115a, 115b and 115c span approximately a distance corresponding to at least the length of the active electrode 104, in a row of axially spaced apertures 115, so that the return electrode 112 is adequately wetted uniformly around the area adjacent the active electrode 104. Discharge apertures 115a, b and c may be limited in number and size due to structural requirements of shaft distal portion 120.

In certain embodiments, the discharge apertures 115a, b and c may be disposed adjacent the active electrode 104 in order to provide a clear path and uniform fluid flow around the shaft distal portion to the active electrode 104. Discharge apertures 115a, b and c are approximately oval in shape to create as large an opening as possible to not hinder fluid flow and to maximize fluid output, and in certain embodiments the size of the discharge aperture may be increased from proximal location to distal location (i.e., from aperture 115a to aperture 115c, so that for example aperture 115c is slightly larger than aperture 115b, and so on). In alternative embodiments, not shown here, and there may be a plurality of axially spaced discharge aperture rows on either side of the active electrode 104. Apertures 115a, 115b and 115c are connected to a fluid supply element as described in later figures, and are operable to transfer conductive fluid from this fluid supply element to the shaft distal portion 120.

The number, size, shape and location of apertures 115a, b and c, as well as the rate of fluid supply determine how much of the return electrode 112 is "wetted" and how uniform the wetted area is. Apertures 115a, b and c may be a variety of shapes such as ovals, elongate slits or circles. Alternative embodiments for the discharge aperture may comprise one elongate slit that may vary in width along its length so as to keep a uniform fluid delivery along the distal portion length. The goal of apertures 115a, b and c is to minimize areas on the return electrode 112 surface that are dry. It is preferable for the return electrode surface to be uniformly wetted to create a more-even electrical field between the active electrode 104 and return electrode 112, so as to create a more reliable and uniform tissue effect. Areas of the return external surface that are relatively dry may induce resistive heating effects and unwanted tissue effect is those areas.

In general, the ratio between the wetted return electrode area and active electrode surface area should be between 2:1 and 10:1, and more optimally around 8:1. Electrode surface area may be defined as the exposed conductive surface of the active electrodes 104. As will be apparent to those of skill in the art, the active electrode surface area depends on the size of the active electrode itself. Additionally, in certain embodiments all surface areas may be further altered or adjusted using coatings or electrical insulation so as to control any active electrode surface area value.

Figure 2E:
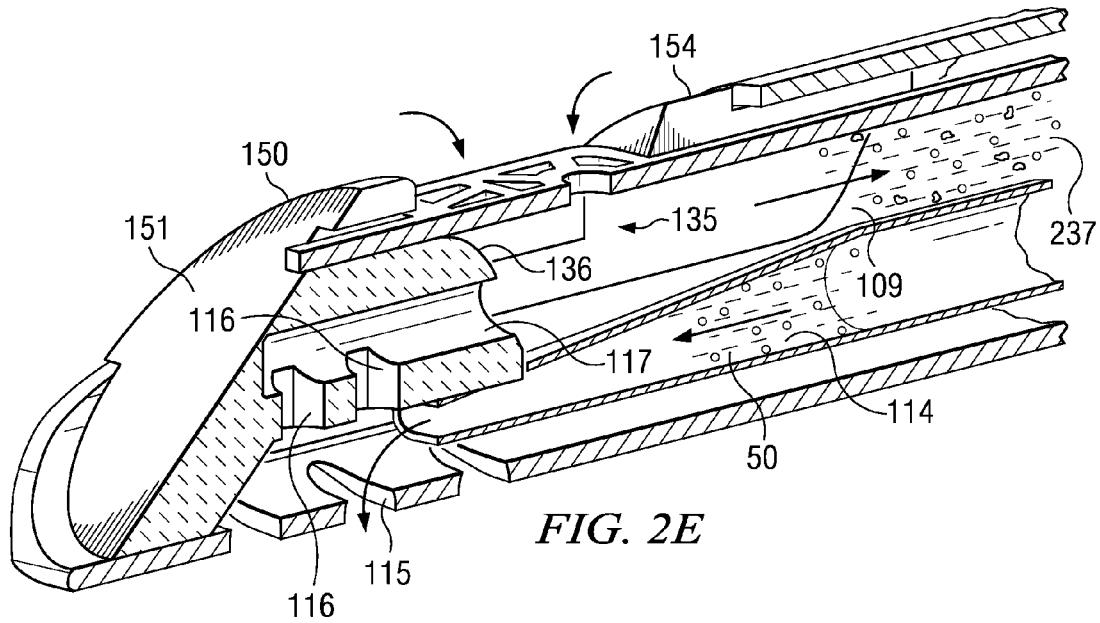
FIG. 2E shows a longitudinal cross-section view of an instrument distal end portion according to at least certain embodiments.

Referring now to FIG. 2E, a cross-section of an embodiment of a shaft distal end portion 120 is shown, with details of the support 150, suction cavity 135 and discharge apertures 115 with additional flushing conduits 116 shown. Support member 150 may be preferably formed from an inorganic material such as a ceramic, or any material capable of insulating the active electrode 104 from the return electrode 112 during application of electrical energy. Insulating electrode support member 150 may be seen in greater detail, having a distal plane 151 preferably angled to ease instrument access to target tissues as explained earlier. Additionally support 150 has a proximal portion 154 generally formed to connect with instrument shaft 100 and return electrode 112 via mechanical means such as press fit, adhesive or snap fits. Support 150 also includes a proximal channel 152 for nesting electrode proximal leg 105 and may fix with said leg 105.

In certain embodiments, support 150 may be characterized by at least one flushing conduit 116 disposed internally within support 150 and fluidly connected with fluid supply 114. Flushing conduits 116 are located adjacent discharge apertures 115 and are operable so that a portion of the conductive fluid supplied preferably flows through the flushing conduit 116 and travels proximally through flushing channel 117 and into suction cavity 135 disposed adjacent active electrode 104. Flushing conduit 116 supplies a portion of fluid, clear of any ablation by-products or tissue fragments to mix with the aspirated by-products that travel through active electrode apertures (130, 131 and 132) in order to reduce the likelihood of clogging of the suction element. The relative size, shapes and locations of flushing conduits 116 relative to the discharge apertures 115 will determine the relative amount of fluid that flows through the at least one flushing conduit 116. Shown here, the at least one flushing conduit 116 is proportionally smaller than discharge apertures 115, and approximately axially offset from discharge apertures 115.

Suction cavity 135 further comprises a distal cavity ramp 136 at the distal end of suction cavity. Applicants have found that suction reduces significantly between the proximal end of suction cavity 135 and distal end, and there may be a dead spot at the most distal portion of suction cavity 135. A ramp or curved slope 136 has been shown to reduce this dead spot and improve suction and flow of the tissue and ablation by-products through electrode apertures 130, 131 and 132 as well as out of the aspiration cavity into the fluid aspiration element 109. Ramp 136 provides a surface that slopes downward, away from active electrode 104 into suction cavity 135 with the upper portion of ramp 136, closest to the active electrode, being more distal and the lower portion of ramp 136 being more proximal and connected with the proximal portion of the aspiration cavity 135, that has the larger cross-sectional width and depth.

Aspiration apertures 130, 131 and 132 are fluidly connected with aspiration or suction cavity 135, which is operable to transport fluid, tissue fragments, and gases 237 from the ablative process away from the target site, and into a fluid aspiration element 109 which may be disposed within shaft 100. Shown here, aspiration element 109 includes shaft 100 for at least a portion of shaft length. In other embodiments, aspiration element 109 may include at least one lumen or tube (not shown) that extends from suction cavity 135 within shaft 100 for a portion of shaft length. Alternatively, electrode support 150 may extend along a portion of the shaft length and connect to an outlet or suction source (neither shown) within instrument handle 204.

Electrically conductive fluid 50 may be supplied via a fluid delivery element, comprising a tube (not shown here) connected with a fluid supply lumen 114. Lumen 114 may be tapered distally, to alter flow velocity or just to fit within distal end portion 120 space requirements. Lumen 114 may supply electrically conductive fluid to discharge apertures 115 and flushing conduits 116. In other embodiments fluid may be supplied though shaft 100, provided the aspiration element is a separate tube or lumen.

Figure 3:
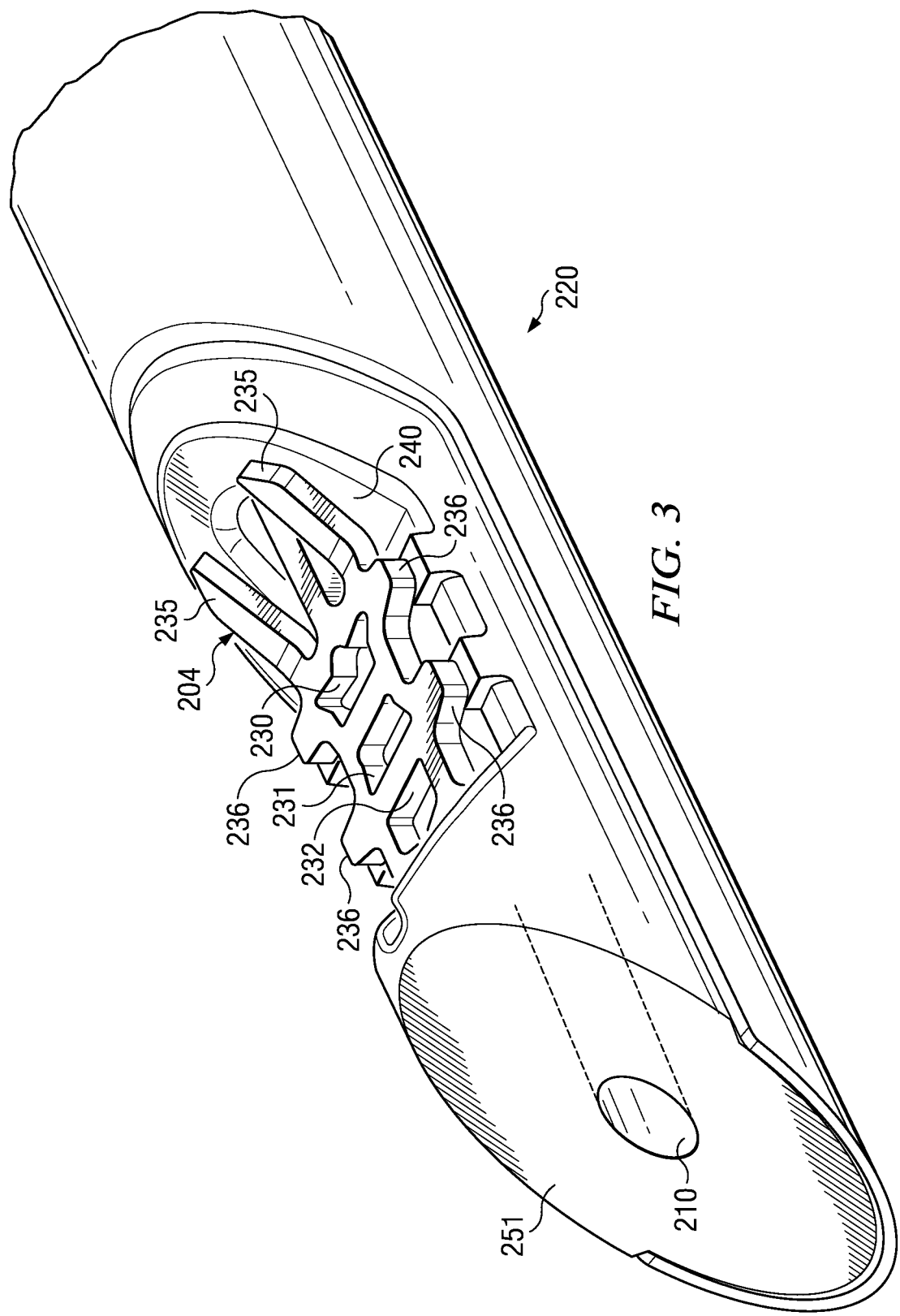
FIG. 3 shows an alternative embodiment of an instrument distal end portion according to at least certain embodiments.

FIG. 3 shows an alternative embodiment for active electrode 204 disposed on instrument shaft distal portion 220. Shaft distal portion 220 is similar to embodiment shown in previous figures, with the exception of active electrode 204 which has at least three axially spaced apertures 230, 231 and 232 disposed though active electrode 204. Additionally active electrode 204 has angled of bent tabs 235 disposed on at least the proximal portion of active electrode 204, as well as lateral tabs 236. These tabs 235 and 236 are electrically connected with active electrode and are operable to reduce any tissue and ablation by-product buildup on either the edges of active electrode 204 or the gaps between electrode and support shelf 240.

The embodiment in FIG. 3 also shows a clearing port 210 that provides a conduit or access to suction cavity 235 disposed beneath the active electrode 204. Clearing port 210 is shown with an opening on the support distal surface 251 and is operable to provide the user access to the suction cavity 235 and fluid aspiration element (not shown here) should tissue or ablation by-products become clogged within element. User may use an appropriately shaped tool to remove said clog.

Figure 4A:
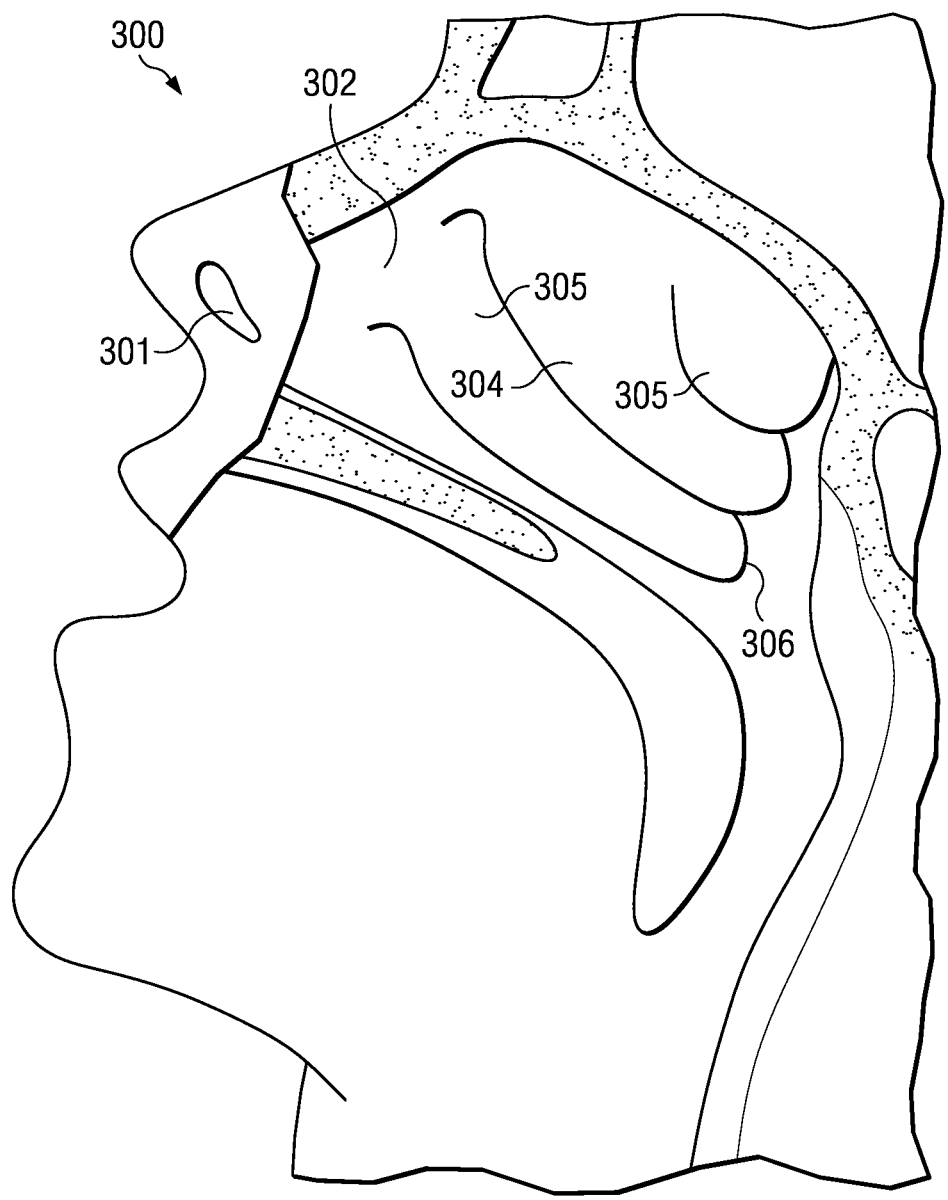
FIG. 4A shows a nasal cavity for potential treatment using an electrosurgical system constructed according to at least certain embodiments.

FIG. 4A illustrates a nasal cavity, being prepared for treatment for enlarged body structures, such as polyps or turbinates, according to the present invention. In these procedures, the polyps, turbinates or other sinus tissue may be ablated or reduced (e.g., by tissue contraction) to clear the blockage and/or prevent further swelling of the turbinates to reestablish normal sinus function. For example, in chronic rhinitis, which is a collective term for chronic irritation or inflammation of the nasal mucosa with hypertrophy of the nasal mucosa, the inferior turbinate may be reduced by ablation or contraction. Alternatively, a turbinectomy or mucotomy may be performed by removing a strip of tissue from the lower edge of the inferior turbinate to reduce the volume of the turbinate. For treating nasal polypi, which comprises benign pedicled or sessile masses of nasal or sinus mucosa caused by inflammation, the nasal polypi may be contracted or shrunk, or ablated by the method of the present invention. For treating severe sinusitis, a frontal sinus operation may be performed to introduce the electrosurgical probe to the site of blockage. The present invention may also be used to treat diseases of the septum, e.g., ablating or resecting portions of the septum for removal, straightening or reimplantation of the septum.

The present invention is particularly useful in reducing enlarged turbinates by volumetrically removing a portion of the turbinates. As shown in FIG. 4A, a patient's nose 300 comprises a nasal cavity 302 having a set of turbinates 305, including a middle nasal concha 304 and an inferior nasal concha 306. The inferior nasal concha 306 generally comprises an anterior portion and a posterior portion. It has been found that treating the inferior nasal concha 306, typically the anterior portion, does not substantially degrade its function. According to the present disclosure, the distal end of probe 90 may be introduced through nasal passage 301 into the nasal cavity 302.

Figure 4B:
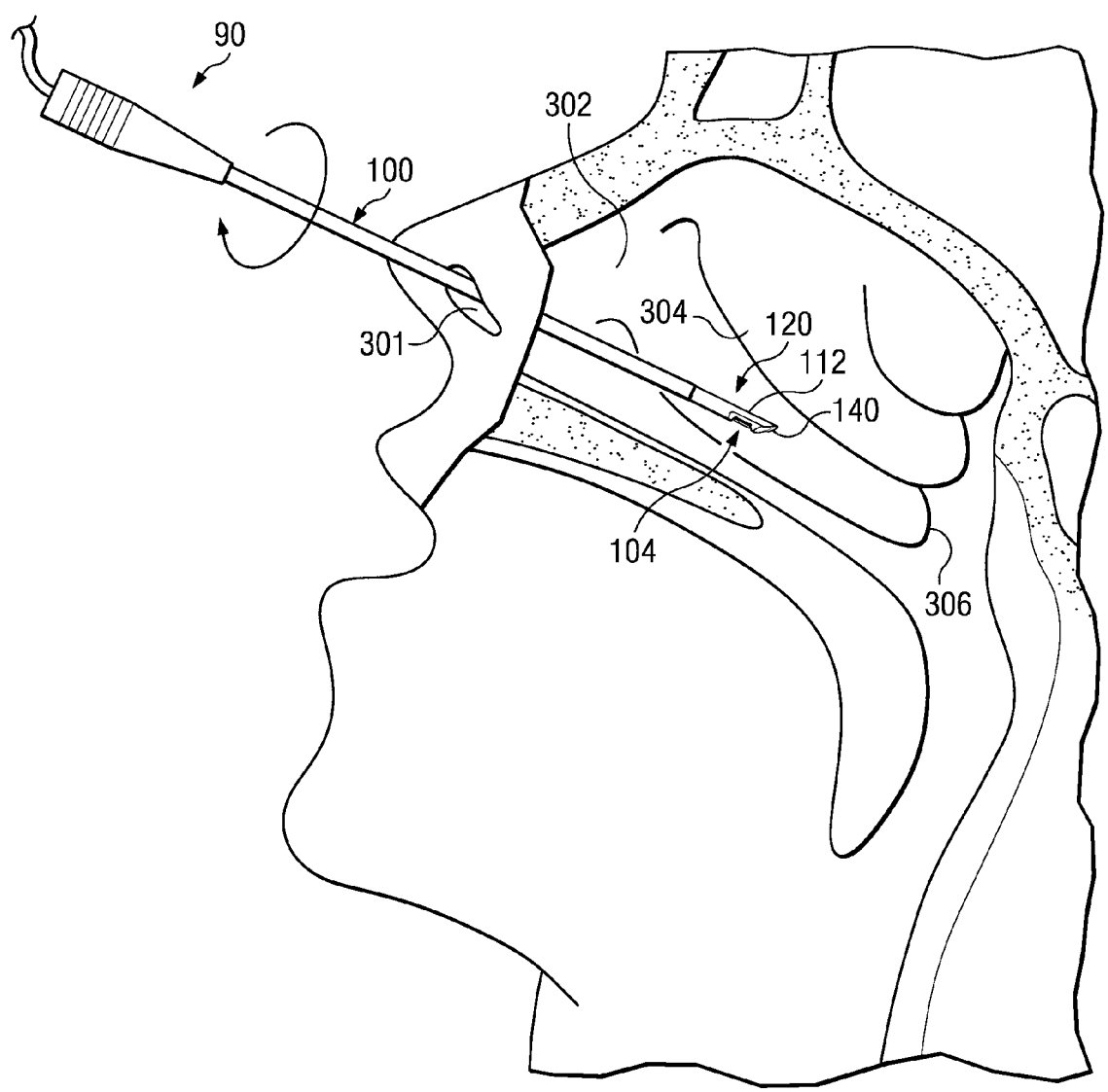
FIG. 4B shows a nasal cavity with an electrosurgical instrument disposed within, the instrument shown according to at least certain embodiments.

FIG. 4B illustrates an exemplary endoscopic sinus surgery according to the teachings in the present disclosure. An endoscope may first be introduced (not shown) through one of the nasal passages 301 to allow the surgeon to view the target site, e.g., the sinus cavities. Shaft 100 may have a bend or curve to facilitate use of both the endoscope and the probe 90 in the same nasal passage (i.e., the handles of the two instruments do not interfere with each other in this embodiment). Alternatively, the endoscope may be introduced transorally through the inferior soft palate to view the nasopharynx.

Alternatively, the endoscope may include a sheath having an inner lumen for receiving the electrosurgical probe shaft 100. In this embodiment, the shaft 100 will extend through the inner lumen to a distal opening in the endoscope. The shaft will include suitable proximal controls for manipulation of its distal end during the surgical procedure.

As shown in FIG. 4B, the probe distal portion 120 is introduced through nasal passage 301 into the nasal cavity 302. Depending on the location of the blockage or swelling, the distal tip 140 will be positioned adjacent the blockage in the nasal cavity 302, or in one of the paranasal sinuses 304, 306. Once the surgeon has reached the point of major blockage or swelling, surgeon may chose to use distal tip 140 to access blocked area through blunt or sharp dissection. Alternatively, the surgeon may chose to use an alternate instrument to make a window to gain access to sinus tissue. Once access has been gained, electrically conductive fluid flow may be initiated by pump 40 such that conductive fluid may be delivered to the distal portion 120. The fluid flows over the return electrode 112 to wet the return electrode surface at the distal end portion of the shaft.

Additionally, by virtue of the fluid pressure provided by the pump 40, the conductive fluid provided into the nasal cavity may have the effect of enlarging the opening for accessing and treating the targeted the sinus tissue. The effect of the fluid under pressure provided within the accessed cavity tissue is to expand the opening and provide additional space within the cavity tissue that allows for effective plasma formation at the active electrode 104. The larger access cavity also enhances the benefit of the active electrode 104 being recessed away from the superior surface 121 of the distal portion 120 of the device. The rate of fluid flow may be controlled by pump 40, or alternatively with a valve (not shown), such that the zone between the tissue and electrode support 150 is constantly immersed or coated with the fluid and the return electrode 112 is sufficiently wetted. The power supply 28 (shown in FIG. 1) is then turned on and adjusted such that a high frequency voltage difference is applied between active electrode 104 and return electrode 112. The electrically conductive fluid provides the conduction path between active electrode 104 and the return electrode 112. Apparatus 90 may then be translated and/or rotated to bore out or core out sinus tissue to reduce or debulk tissue mass.

Depending on the procedure, the surgeon may rotate and/or translate the electrode 104 relative to the turbinate tissue to form holes, channels, stripes, divots, craters or the like within the turbinate. In addition, the surgeon may purposely create some thermal damage within these holes, or channels to form scar tissue that will inhibit the turbinate from swelling after the procedure. In one embodiment, the physician axially rotates the shaft distal portion 120 within the turbinate tissue as the tissue is volumetrically removed to form one or more holes in the turbinate, typically having a diameter of less than 5 mm, preferably less than 2 mm. The active electrode 104 may be generally sized to be approximately the length of an average body structure to be treated. For example a turbinate may typically be approximately 10-15 mm long and an active electrode 105 may be approximately 5-20 mm in length, to accommodate the particular target turbinate. Instrument 90 and active electrode length is operable to treat tissue during a predominantly rotational movement with minimal advancing and retracting. This allows the surgeon to plan for a more reliable amount of removed or treated tissue. In another embodiment, the physician may also axially translate the distal portion 120 into the turbinate tissue as the tissue is volumetrically removed to form one or more holes in the turbinate, typically having a diameter of less than 2 mm, preferably less than 1 mm. Shaft distal portion 120 may be sized so as to access the nasal cavity and form these holes, and therefore would be between 1-5 mm in diameter and more preferably approximately 2 mm. In another embodiment, the physician may translate the electrode 104 across the outer surface of the turbinates to form one or more channels or troughs.

Another advantage of the present invention is the ability to precisely ablate channels or holes within the turbinates without causing necrosis or thermal damage to the underlying and surrounding tissues, nerves (e.g., the optic nerve) or bone. In addition, the voltage delivered by power supply 28 can be controlled so that the energy directed to the target site is insufficient to ablate bone or adipose tissue (which generally has a higher impedance than the target sinus tissue). In this manner, the surgeon can literally clean the tissue off the bone, without ablating or otherwise effecting significant damage to the bone.

Figure 5:
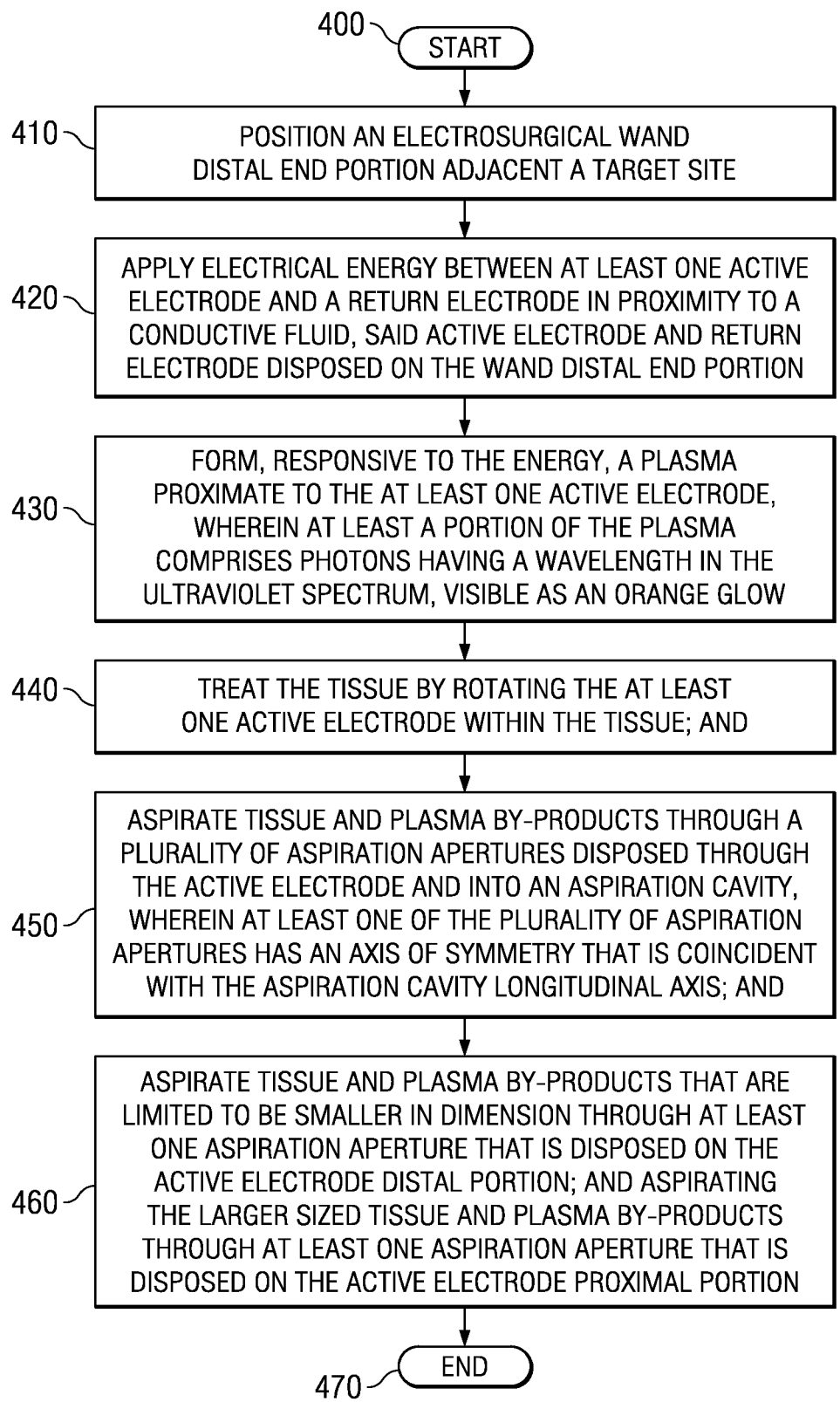
FIG. 5 shows a flow diagram of a medical procedure, using a system according to at least certain embodiments.

Referring now to FIG. 5, a method (400) for treating tissue in accordance with at least some of the embodiments described herein is illustrated, including the steps of: positioning (410) an electrosurgical wand distal end portion adjacent to the target site, followed by applying (420) electrical energy between at least one active electrode and a return electrode in proximity to a conductive fluid, said active electrode and return electrode disposed on an electrosurgical wand; followed by forming (430), responsive to the energy, a plasma proximate to the at least one active electrode; and treating (440) the tissue by rotating the at least one active electrode within the tissue; and aspirating (450) tissue and plasma by-products through a plurality of aspiration apertures disposed through the active electrode and into an aspiration cavity, wherein at least one of the plurality of aspiration apertures has an axis of symmetry that is coincident with and parallel to the aspiration cavity longitudinal axis; and finally aspirating (460) tissue and plasma by-products that are limited to be smaller in dimension through at least one aspiration aperture that is disposed on the active electrode distal portion; and aspirating the larger sized tissue and plasma by-products through at least one aspiration aperture that is disposed on the active electrode proximal portion.

During the step of forming, at least a portion of the plasma may be visible to the user as an orange glow, as the plasma may comprise photons having a wavelength in the ultraviolet spectrum. This orange glow may be used as a position indicator and aid the user in ensuring that the target area is correct and the plasma is forming. In particular, the orange glow emitted by the plasma may be visible to the user while looking directly into the body cavity where treatment may be occurring, or by observing the glow through the skin or anatomical structure surrounding the body cavity. The visual observation of that plasma in the form of emitted visible wavelengths may provide valuable information for the user to make note of the position of the device, and to specifically make adjustments in response to the observed location and depth of the active electrodes of the device while the device is translated, rotated, or otherwise positioned and adjusted during treatment of the target tissue. Additionally, this method may also include the step of flowing a conductive fluid within a fluid delivery lumen disposed within the electrosurgical wand, wherein the conductive fluid is discharged through a plurality of discharge apertures disposed through the return electrode. A portion of this conductive fluid may also be directed through at least one flushing conduit to flush the aspiration cavity. An alternate source of clear fluid may be used to help flush the aspirated products and aid in keeping the aspirating element clear of clogs and debris. Target tissue may include blockages within the nasal cavity or a paranasal sinus of the patient or more specifically swollen tissue, turbinates, polyps, neoplasms and swollen mucus membranes lining an inner surface of the nasal cavity.

Other tissues outside of the nasal cavity may also be treated, such as prostate, heart or any other body structure. The high frequency voltage may be altered or sufficient as is to effect hemostasis of severed blood vessels within the tissue during the supplying step. The electrosurgical probe may further comprise a distal tip, operable to bluntly dissect tissue or create a window into a body structure.

Although only a few embodiments of the present invention have been described, it should be understood that the present invention may be embodied in many other specific forms without departing from the spirit or the scope of the present invention. Therefore, the present examples are to be considered as illustrative and not restrictive, and the invention is not to be limited to the details given herein, but may be modified within the scope of the appended claims.

What is claimed is:

1. An electrosurgical apparatus for treating tissue at a target site comprising:
    an elongate housing having a longitudinal axis, and having a handle end and a distal portion;
    an electrode support disposed on the housing distal portion;
    the electrode support having an aspiration cavity with an opening; and
    an active screen electrode disposed on the electrode support and covering the aspiration cavity opening, the active electrode having a plurality of apertures fluidly connected with the aspiration cavity; and
    a return electrode disposed on the distal portion, the return electrode encircling at least a portion of the electrode support;
    the aspiration cavity having a cavity ramp operable to direct the flow of any fluid, tissue and ablation byproducts disposed adjacent the cavity ramp in a proximal direction.

2. The electrosurgical apparatus of claim 1, wherein the return electrode comprises at least one discharge aperture.

3. The electrosurgical apparatus of claim 1, wherein the return electrode comprises a distal dissection edge that extends beyond a distal end of the electrode support.

4. The electrosurgical apparatus of claim 2, wherein the at least one discharge aperture is disposed on an inferior surface of the return electrode.

5. The electrosurgical apparatus of claim 4, wherein the at least one discharge aperture is fluidly coupled to a second fluid conduit, the second fluid conduit disposed within the elongate housing.

6. The electrosurgical apparatus of claim 5, wherein the second fluid conduit is fluidly coupled to a pump and a fluid supply element and is operable to deliver electrically conductive fluid to the at least one discharge aperture to an exterior surface of the housing distal portion.

7. The electrosurgical apparatus of claim 1 wherein the cavity ramp is oriented to slope up towards the active electrode, as transitioning from proximal to distal.

8. The electrosurgical apparatus of claim 1, wherein a portion of the aspiration cavity under a proximal portion of the active electrode has a maximum cross-sectional width.

9. The electrosurgical apparatus of claim 1 wherein the plurality of apertures comprises a maximum aperture, larger than all other aspiration apertures associated with the active electrode, the maximum aperture having an axis of symmetry aligned with a longitudinal axis of the aspiration cavity.

10. An electrosurgical apparatus for treating tissue at a target site comprising:
    a shaft having a proximal end and a distal portion, the distal portion having a return electrode and an electrode support defining a fluid aspiration cavity within the electrode support; and
    an active electrode disposed on the electrode support, wherein the active electrode has a proximal portion and an electrode distal portion and a plurality of aspiration apertures through said active electrode, said plurality of aspiration apertures fluidly connected to the fluid aspiration cavity;
    the plurality of apertures having a first aperture, larger than all other aspiration apertures disposed on the active electrode the first aspiration aperture being disposed towards the proximal portion of the electrode and having an axis of symmetry that aligns with a longitudinal axis of the fluid aspiration cavity.

11. The electrosurgical apparatus of claim 10, wherein the active electrode is oriented parallel to a longitudinal axis of the shaft distal portion, and recessed away from a superior surface of the shaft distal portion.

12. The electrosurgical apparatus of claim 10 wherein the shaft distal portion further comprises a distal tip spaced distally from the active electrode, a distal portion of the return electrode defining a portion of the distal tip, and wherein the distal tip has an acute angle relative to a shaft long axis.

13. The electrosurgical apparatus of claim 10 wherein the fluid aspiration cavity has a distal ramp portion.

14. The electrosurgical apparatus of claim 10, wherein the return electrode at least partially encircles the active electrode and extends distally further than the active electrode.

15. The electrosurgical apparatus of claim 10 further comprising a fluid supply element disposed within the electrode support and operable to deliver an electrically conductive fluid to the electrode support, and wherein the return electrode has a plurality of discharge apertures fluidly connected with the fluid supply element, said discharge apertures disposed on an inferior outer surface of the return electrode, operable so that the fluid electrode, operable so that the fluid flows from the supply element and through the discharge apertures to the outer surface of the return electrode.

16. The electrosurgical apparatus of claim 15 wherein the plurality of discharge apertures comprise at least one row of axially spaced discharge apertures.

17. The electrosurgical apparatus of claim 15, wherein the discharge apertures vary in size, and wherein larger sized discharge apertures are disposed distal to the smaller sized discharge apertures.

18. The electrosurgical apparatus of claim 15 wherein the fluid supply element comprises at least one fluid delivery lumen extending within at least a portion of the shaft length and wherein the fluid supply element has an outlet within the shaft distal portion.

19. The electrosurgical apparatus of claim 15 further comprising at least one flushing conduit disposed within the electrode support, the conduit having a first end disposed within the electrode support and coupled to the fluid supply element and a second end disposed within the electrode support coupled to the aspiration cavity.

20. The electrosurgical apparatus of claim 10 wherein the shaft distal portion is sized for delivery into a paranasal cavity of a patient.

21. The electrosurgical apparatus of claim 10 wherein the apparatus is operable to treat tissue selected from a group consisting of polyps, turbinates, neoplasms, or swollen mucous membranes.

22. The electrosurgical apparatus of claim 10 wherein the at least one active electrode comprises a screen electrode, said electrode further comprising a distal leg operable to engage with the electrode support, and wherein said electrode further comprises a proximally extending leg operable to supply electrical energy to the active electrode.

23. The electrosurgical apparatus of claim 10 further comprising at least one clearing port having an opening on a shaft distal portion outer surface and connected with the fluid aspiration cavity, said port operable to provide access to the cavity to remove clogs within cavity and fluid aspiration element when needed.

24. The electrosurgical apparatus of claim 10, wherein the active electrode further comprises at least one tab extending from the active electrode and electrically connected with the active electrode, the at least one tab being operable to minimize tissue buildup at the edges of the active electrode adjacent the at least one tab.

25. An electrosurgical apparatus for removing tissue from a body structure comprising:
    a shaft having a proximal end, a distal portion, and a distal tip, the shaft distal portion having a tubular insulating support member with
    at least one recessed support shelf;
    a fluid supply disposed within the support member;
    at least one aspiration cavity disposed within said support member and adjacent the support shelf, and
    at least one flushing conduit disposed within the support member, the conduit having a first end disposed within the support member coupled to the fluid supply element and a second end disposed within the support member coupled to the at least one aspiration cavity; and
    a return electrode encircling at least a portion of the tubular support member; and
    an active electrode disposed on the recessed support shelf;
    wherein the return electrode has at least one discharge aperture disposed through said return electrode and fluidly connected with the fluid supply element, so that a portion of an electrically conductive fluid delivered through the supply element flows from the fluid supply element through at least one discharge aperture to an exterior surface of the distal portion and a portion of the fluid flows from the fluid supply element through the flushing conduit into the aspiration cavity.

26. The electrosurgical apparatus of claim 25, wherein the return electrode further comprises a plurality of discharge apertures arranged in at least one row of axially spaced apertures disposed on an inferior side of the return electrode.

27. The electrosurgical apparatus of claim 25, wherein the fluid supply element contains an electrically conductive fluid.

28. The electrosurgical apparatus of claim 25, wherein the support member further comprises at least one opening disposed distal to the support shelf, operable to engage with an active electrode distal leg, and at least one channel disposed proximal to the support shelf, operable to support an active electrode proximal leg.

29. The electrosurgical apparatus of claim 25, wherein the distal tip comprises a leading edge, operable to dissect body tissue and create a window into the body structure.

30. The electrosurgical apparatus of claim 29 wherein the distal tip leading edge is a portion of the return electrode.

31. The electrosurgical apparatus of claim 25 wherein the support member further comprises a clearing port, operable to provide access from an outer surface of a support member to the aspiration cavity and aspiration element fluidly connected with the aspiration cavity, so as to be able to manually remove clogs within the aspiration element.

\* \* \* \* \*